(12) United States Patent
Chu et al.

(10) Patent No.: US 7,611,708 B2
(45) Date of Patent: *Nov. 3, 2009

(54) METHODS OF THERAPY FOR B-CELL MALIGNANCIES USING ANTAGONIST ANTI-CD40 ANTIBODIES

(75) Inventors: Keting Chu, Burlingame, CA (US); Lorianne K. Masuoka, Oakland, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/246,029

(22) Filed: Oct. 6, 2008

(65) Prior Publication Data

US 2009/0081242 A1    Mar. 26, 2009

Related U.S. Application Data

(63) Continuation of application No. 11/849,107, filed on Aug. 31, 2007, now Pat. No. 7,445,780, which is a continuation of application No. 10/380,223, filed as application No. PCT/US01/30963 on Oct. 2, 2001, now Pat. No. 7,288,252.

(60) Provisional application No. 60/237,556, filed on Oct. 2, 2000.

(51) Int. Cl.
*A61K 39/395* (2006.01)
*C07K 16/28* (2006.01)

(52) U.S. Cl. ............... 424/153.1; 424/130.1; 424/133.1; 424/138.1; 424/141.1; 424/143.1; 424/144.1; 424/155.1; 424/173.1; 424/174.1; 424/178.1; 424/183.1; 530/387.1; 530/387.3; 530/387.7; 530/388.1; 530/388.2; 530/388.22; 530/388.7; 530/388.73; 530/388.8; 530/391.1; 530/391.7

(58) Field of Classification Search .................. None
See application file for complete search history.

(56) References Cited

U.S. PATENT DOCUMENTS

| | | | |
|---|---|---|---|
| 4,355,023 A | 10/1982 | Ehrlich et al. |
| 4,689,299 A | 8/1987 | Insel et al. |
| 4,886,796 A | 12/1989 | Eichner et al. |
| 4,923,872 A | 5/1990 | Kostlan et al. |
| 5,068,223 A | 11/1991 | Lipsky et al. |
| 5,100,899 A | 3/1992 | Calne |
| 5,182,368 A | 1/1993 | Ledbetter et al. |
| 5,674,492 A | 10/1997 | Armitage et al. |
| 5,677,165 A | 10/1997 | De Boer et al. |
| 5,693,762 A | 12/1997 | Queen et al. |
| 5,874,082 A | 2/1999 | de Boer |
| 7,288,252 B2 | 10/2007 | Chu et al. |
| 7,445,780 B2 | 11/2008 | Chu et al. |
| 2002/0028178 A1 | 3/2002 | Hanna et al. |
| 2002/0142358 A1 | 10/2002 | Mikayama et al. |
| 2003/0059427 A1 | 3/2003 | Force et al. |
| 2008/0075727 A1 | 3/2008 | Chu et al. |

FOREIGN PATENT DOCUMENTS

| | | |
|---|---|---|
| EP | 0 434 879 A1 | 7/1991 |
| EP | 0 555 880 A2 | 8/1993 |
| EP | 0 945 465 A1 | 9/1999 |
| WO | WO 90/07861 A1 | 7/1990 |
| WO | WO 92/00092 A1 | 1/1992 |
| WO | WO 93/08207 A1 | 4/1993 |
| WO | WO 93/11794 A1 | 6/1993 |
| WO | WO 94/01547 A2 | 1/1994 |
| WO | WO 94/04570 A1 | 3/1994 |
| WO | WO 95/09653 A1 | 4/1995 |
| WO | WO 96 34096 A1 | 10/1996 |
| WO | WO 00/75348 A1 | 12/2000 |
| WO | WO 01/24823 A1 | 4/2001 |
| WO | WO 01/34649 A2 | 5/2001 |
| WO | WO 01/83755 A2 | 11/2001 |

OTHER PUBLICATIONS

Green, L.L., "Antibody Engineering via Genetic Engineering of the Mouse: XenoMouse Strains Are a Vehicle for the Facile Generation of Therapeutic Human Monoclonal Antibodies," *Journal of Immunological Methods*, 1999, pp. 11-23, vol. 231.

An, S., and K.A. Knox et al., "Ligation of CD40 Rescues Ramos-Burkitt Lymphoma B Cells From Calcium Ionophore and Antigen Receptor-Triggered Apoptosis by Inhibiting Activation of the Cysteine Protease CPP32/Yama and Cleavage of its Substrate PARP," *FEBS Letters*, 1996, pp. 115-122, vol. 386.

Armitage, R.J., et al., "Molecular and Biological Characterization of a Murine Ligand for CD40," *Nature*, 1992, pp. 80-82, vol. 357.

(Continued)

*Primary Examiner*—Phillip Gambel
(74) *Attorney, Agent, or Firm*—Lisa Alexander; Leslie Henry

(57) ABSTRACT

Methods of therapy for B-cell malignancies are provided. The methods comprise administering a therapeutically effective amount of an antagonist anti-CD40 antibody or antigen-binding fragment thereof to a patient in need thereof. The antagonist anti-CD40 antibody or antigen-binding fragment thereof is free of significant agonist activity when the antibody binds a CD40 antigen on a normal human B cell, exhibits antagonist activity when the antibody binds a CD40 antigen on a malignant human B cell, and can exhibit antagonist activity when the antibody binds a CD40 antigen on a normal human B cell. Antagonist activity of the anti-CD40 antibody or antigen-binding fragment thereof beneficially inhibits proliferation and/or differentiation of malignant human B cells.

9 Claims, 6 Drawing Sheets

OTHER PUBLICATIONS

Axcrona, K., et al., "Regulation of B Cell Growth and Differentiation Via CD21 and CD40," *Eur. J. Immunol.* 1996, pp. 2203-2207, vol. 26.

Bajorath, J. et al., "Construction and Analysis of a Detailed Three-Dimensional Model of the Ligand Binding Domain of the Human B Cell Receptor CD40," *Proteins: Structure, Function and Genetics*, 1997, pp. 59-70, vol. 27.

Banchereau, J. et al., "Long-Term Human B Cell Lines Dependent on Interleukin-4 and Antibody to CD40," *Science*, Jan. 4, 1991, pp. 70-72, vol. 251.

Banchereau et al., "Growing Human B Lymphocytes in the CD40 System," *Nature*, 1991, pp. 678-679, vol. 353.

Barr, T.A., and A.W. Heath, "Functional Activity of CD40 Antibodies Correlates to the Position of Binding Relative to CD154," *Immunology*, 2001, pp. 39-43, vol. 102.

Benoit, N. E. And W.F. Wade, "Increased Inhibition of Proliferation of Human B Cell Lymphomas Following Ligation of CD4- and Either CD19, CD20 CD95 or Surface Immunoglobulin," *Immunopharmacology*, 1996, pp. 129-139, vol. 35.

Berzofsky, J.A. and I.J. Berkower, "Immunogenicity and Antigen Structure," *Fundamental Immunology*, 1993, Chapter 8, p. 242, Raven Press, NY.

Chothia, C. and A.M. Lesk, "Canonical Structures for the Hypervariable Regions of Immunoglobulins," *J. Mol. Biol.*, 1987, pp. 901-917, vol. 196.

Claassen, J.J. et al., "Mononuclear Cells from Patients with the Hyper-IgE Syndrome Produce Little IgE When They Are Stimulated with Recombinant Human Interleukin-4," *Journal Allergy Clin., Immunol*, 1994, pp. 713-721, vol. 88.

Clark, E.A. and J.A. Ledbetter, "Activation of Human B Cells Mediated Through Two Distinct Cell Surface Differentiation Antigens, Bp35 and Bp50," *Proc. Natl. Acad. Sci.*, 1986, pp. 4494-4498, vol. 83, USA.

Clark et al., "Association Between IL-6 and CD40 Signaling ILO-6 Induces Phosphorylation of CD40 Receptors," *J. Immunol.*, 1990, pp. 1400-1416, vol. 145, No. 5.

Cosimi, A.B. et al . "Use of Monoclonal Antibodies to T-Cell Subsets for Immunologic Monitoring and Treatment in Recipients of Renal Allografts," *N. Eng. J Med.*, Aug. 6, 1981, pp. 308-313, vol. 305, No. 6.

de Boer, M. et al. "Generation of Monoclonal Antibodies to Human Lymphocyte Cell Surface Antigens Using Insect Cells Expressing Recombinant Proteins," *J. Immunol, Meth.*, 1992, pp. 15-23, vol. 152.

de Boer, M. et al., "Functional Characterization of a Novel Anti-B7 Monoclonal Antibody," *Eur. J Immunology*, 1992, pp. 3071-3075, vol. 22, No. 12.

DeFranco, A.L. et al. "Separate Control of B Lymphocyte Early Activation and Proliferation in Response to Anti-IgM Antibodies," *Journal of Immunology*, 1985, pp. 87-94, vol. 135, No. 1.

Dharakul, T. et al., "Immunization with Baculovirus-Expressed Recombinant Rotavirus Proteins VP1, VP4, VP6 and VP7 Induces CD8+ T Lymphocytes That Mediate Clearance of Chronic Rotavirus Infection in SCID Mice," *J Virol.*, 1991, pp. 5928-5932, vol. 65, No. 11.

DiSanto, J.P. et al. "Generation of Anti-Human CD8B-Specific Antibodies Using Transfectants Expressing Mixed-Species CD8 Heterodimers," *J. Immunol. Methods*, 1991, pp. 123-131, vol. 141.

Edgington, S.M., "How Sweet It Is: Selectin-Mediating Drugs," *Biotechnology*, 1992, pp. 383-389, vol. 10.

Ellmark, P. et al., "Modulation of the CD4O-CD40 Ligand Interaction Using Human Anti-CD40 Single-chain Antibody Fragments Obtained from the n-CoDeR Phage Display Library," *Immunology*, 2002, pp. 456-463, vol. 106.

Francisco, J.A. et al., "Agonistic Properties and in Vivo Antitumor Activity of the Anti-CD40 Antibody SGN-14," *Cancer Research*, Jun. 15, 2000, pp. 3225-3231, vol. 60.

Freedman, A.S. et al., "B7, A B Cell-Restricted Antigen that Identifies Preactivated B Cells," *Journal of Immunology*, 1997, pp. 3260-3267, vol. 139, No. 10.

Freeman, G.J. et al., "Cloning of B7-2: A CTLA-4 Counter-Receptor That Costimulates Human T Cell Proliferation," *Science*, 1993, pp. 909-911, vol. 262.

Freeman, G.J. et al., "B7, A New Member of the Ig Superfamily with Unique Expression on Activated and Neoplastic B Cells," *Journal of Immunology*, 1989, pp. 2714-2722, vol. 143, No. 8.

Funakoshi, S. et al., "Differential In Vitro and In Vivo Antitumor Effects Mediated by Anti-CD40 and Anti-CD20 Monoclonal Antibodies Against Human B-Cell Lymphomas," *Journal of Immunology*, 1996, pp. 93-101, vol. 19, No. 2.

Funakoshi, S., et al., "Inhibition of Human B-Cell Lymphoma Growth by CD450 Stimulation," *Blood*, 1994, pp. 2787-2794, vol. 83, No. 10.

Furman, R.R., *et al.*, "Modulation of NF-κB Activity and Apoptosis in Chronic Lymphocytic Leukemia B Cells," *Journal of Immunology*, 2000, pp. 2200-2206, vol. 164.

Garrone, P. et al., "Fas Ligation Induces Apoptosis of CD40-Activated Human B Lymphocytes," *J. Exp. Med.*, 1995, pp. 1265-1273, vol. 182.

Garrone, P. et al., "mAb 104, A New Monoclonal Antibody, Recognizes the B7 Antigen That is Expressed On Activated B Cells and HTLV-1 Transformed T Cells" *Immunology*, 1990, pp. 531-535, vol. 69.

Gascan, H. et al., "Anti-CD40 Monoclonal Antibodies or CD4 T Cell Clones and IL-4 Induce IgG4 and IgE Switching in Purified Human B Cells Via Different Signaling Pathways," *Journal of Immunology*, 1991, pp. 8-13, vol. 147, No. 1.

Gauchat. J.-F. et al., "Modulation of IL-4 Induced Germline E RNA Synthesis in Human B Cells By Tumor Necrosis Factor-a, Anto-CD40 Monoclonal Antibodies Or Transforming Growth Factor-13 β Correlates With Levels of IgE Production," *International Immunology*, 1991, pp. 397-406, vol. 4, No. 3.

Golub, E.S.,"Immunology A Synthesis," *Sinauer Assoc. Inc.*, 1987, pp. 19-20, Sunderland, MA.

Gordon, J. et al., "Resting B Lymphocytes Can Be Triggered Directly Through the CDw40 (Bp50) Antigen, A Comparison With IL-4 Mediated Signaling," *Journal of Immunology, 1988*, pp. 1425-1430, vol. 140, No. 5.

Greiner, A. et al., "Low Grade B Cell Lymphomas of Mucosa-Associate Lymphoid Tissue (MALT-Type) Require CD40-Mediated Signaling and Th2-Type Cytokines for In Vitro Growth and Differentiation," *American Journal of Pathology*, 1997, pp. 1583-1593, vol. 150, No. 5.

Gruber et al., "Anti-CD45 Inhibition of Human B Cell Proliferation Depends On The Nature of Activation Signals and the State of B Cell Activation", *J. Immunol.*, 1989, pp. 4144-4152, vol. 142, No. 12.

Gulbins, E. et al., "Activation of the Ras Signaling Pathway by the CD40 Receptor," *Journal of Immunology*, 1996, pp. 2844-2850, vol. 157.

Hager, A.C.M. et al., "Affinity and Epitope Profiling of Mouse Anti-CD40 Monoclonal Antibodies," *Scandanavian Journal of Immunology*, 2003, pp. 517-524, vol. 57.

Hanes, J. et al., *Nature Biotechnology*, 2000, pp. 1287-1292, vol. 18.

Harris, J. et al., "Therapeutic Antibodies-The Coming of Age," *Tibtech*, 1993, pp. 42-44, vol. 11.

Jabara, H.H. et al., "CD40 and IgE: Synergism between Anti-CD40 Monoclonal Antibody and Interleukin 4 in the Induction of IgE Synthesis by Highly Purified Human B Cells," *J. Exp. Med.*, 1990, pp. 1861-1864, vol. 172.

Janeway, C.A. et al., *Immunobiology*, 6th Edition, 2005, Garland, Science, NY; see pp. 446-449,.

Jenkins, M.K. and R.H. Schwartz, "Antigen Presentation by Chemically Modified Splenocytes Induces Antigen-Specific T Cell Unresponsiveness in Vitro and in Vivo," *Journal of Experimental Medicine*, 1987, pp. 302-319, vol. 165.

June, C.H. et al., "Role of the CD28 Receptor in T-Cell Activation," *Immunology Today*, 1990, pp. 211-216, vol. 11, No. 6.

Jung, L.K.L. And S.M. Fu, "Selective Inhibition of Growth Factor-Dependent Human B Cell Proliferation by Monoclonal Antibody AB1 to an Antigen Expressed by Activated B Cells," *J. Exp. Med.*, 1984, pp. 1919-1924, vol. 160.

Kabat, E.A. et al., "Sequences of Proteins of Immunological Interest, Tabulation and Analysis of Amino Acid and Nucleic Acid Sequences of Precursors, V-Regions, C0-Regions, J-Chain, β$_2$-Microglobulins, Major Histocompatibility Antigens, Thy-1, Complement, C-Reactive Protein, Thymopoietin, Post-gamma Globulin, and α₂-Macroglobulin," *Sponsored Through Contract NO1-RR-8- 2118 By Components of the National Institutes of Health*, 1983, Bethesda, MD.

Kahan, B.D., "Immunosuprressive Therapy," *Curr. Opin Immunology*, 1992, pp. 553-560, vol. 4.

Karlsson, P., et al., "Selection of Human Single Chain Antibodies Against CD40," *Immunology Letters*, 2000, p. 161, vol. 73, Nos. 2-3.

Knight, D.M. et al., "The Immunogenicity of the 7E3 Murine Monoclonal FAB Antibody Fragment Variable Region is Dramatically Reduced in Humans by Substitution of Human for Murine Constant Regions," *Molecular Immunology*, 1995, pp. 1271-1281, vol. 32, No. 16.

Kriegler, M. et al., "A Novel Form of TNF/Cachectin is a Cell Surface Cytotoxic Transmembrane Protein: Ramifications for the Complex Physiology of TNF," *Cell*, 1988, pp. 45-53, vol. 53.

Kwekkeboom, J.,et al., "CD40 Plays An Essential Role in the Activation of Human B Cells by Murine EL4B5 Cells," *Immunology*, 1993, pp. 439-444, vol. 79, No. 3.

Lane, P. et al., "Activated Human T Cells Express a Ligand for the Human B Cell-Associated Antigen CD40 which Participated in T Cell-Dependent Activation of B Lymphocytes," *Eur. J. Immunol.*, 1992, pp. 2573-2578, vol. 22.

Lee, C.V. et al., *J. Mol. Biol.*, 2004, pp. 1073-1093, vol. 340.

Linsley et al., "CTLA-4 is a Second Receptor for the B Cell Activation Antigen B7," *J. Exp. Med.*, 1991, pp. 561-569, vol. 174.

Longo, D., et al., "Inhibition of Human B-Cell Lymphoma Growth by Soluble Recombinant Human CD40 Ligand," *The FASEB Journal*, 1995, p. A205, vol. 9, No. 3.

Miller, L.K. "Chapter 23: Baculoviruses for Foreign Gene Expression in Insect Cells," *Vectors: A Survey of Molecular Cloning Vectors and Their Uses*, 1988, pp. 457-465, Butterworths Publishers.

Muraguchi, A. et al., "Sequential Requirements for Cell Cycle Progression of Resting Human B Cells After Activation by Anti-Ig.," *The Journal of Immunology*, 1984, pp. 176-180, vol. 132, No. 1.

Noelle, R. and E.C. Snow et al., "T Helper Cells," *Current Opinion in Immunology*, 1992, pp. 333-337, vol. 4.

Paulie, S. et al., "The Human B Lymphocyte and Carcinoma Antigen, CDw40, is a Phosphoprotein Involved in Growth Signal Transduction," *J. Immunol.*, 1989, pp. 590-595, vol. 142, No. 2.

Planken, E.V. et al., "Proliferation of B Cell Malignancies in all Stages of Differentiation upon Stimulation in the CD40 System," *Leukemia*, 1996, pp. 488-493, vol. 10.

Ross, A.H. et al., "Characterization of Nerve Growth Factor Receptor in Neural Crest Tumors Using Monoclonal Antibodies," *Proc. Natl. Acad. Sci.*, 1984, pp. 6681-6685, vol. 81, U.S.A.

Rousset, F. et al., "Cytokine-Induced Proliferation and Immunoglobulin Production of Human B. Lymphocytes Triggered through Their CD40 Antigen," *J. Exp. Med.*, 1991, pp. 705-710, vol. 173.

Sato et al., "Biological Effects in Vitro of Monoclonal Antibodies to Human Epidermal Growth Factor Receptors," *Mol. Biol. Med.*, 1983, pp. 511-529, Vo. 1.

Schwabe, R.F. et al., "Modulation of Soluble CD40 Ligand Bioactivity with Anti-CD40 Antibodies," *Hybridoma*, 1997, pp. 217-226, vol. 16, No. 3.

Sekine, H. et al., "Expression of Human Papillomavirus Type 6b E2 Gene Product With DNA-Bindng Activity in Insect (Bombyx Mori) Cells Using a Baculovirus Expression Vector," *Gene*, 1988, pp. 187-193, vol. 65, No. 2.

Smith, G.E. et al., "Modification and Secretion of Human Interleukin 2 Produced in Insect Cells by a Baculovirus Expression Vector," *Proc. Natl. Acad. Sci.*, 1985, pp. 8404-8408, vol. 82, USA.

Splawski, J.B. et al., "Immunoregulatory Role of CD40 In Human B Cell Differentiation," *Journal of Immunology*, 1993, 1276-1285, vol. 150.

Takehara, K.et al., "Co-Expression of the Hepatitis B Surface and Core Antigens Using Baculovirus Multiple Expression Vectors," *J. gen. Virol.*, 1988, pp. 2763-2777, vol. 69.

Tanaka, Y. et al., "Distinct Reactivities of Four Monoclonal Antibodies with Human Interleukin 2 Receptor," *Microbial. Immunol.*, 1985, pp. 959-972, vol. 29, No. 10.

Tong, A.W. and M.J. Stone, "CD40 and the Effect of Anti-CD4O-Bindingon Human Multiple Myeloma Clonogenicity," *Leukemia and Lymphoma*, 1996, pp. 1-8, vol. 21.

Tsuchiyama, L. et al., "Synergy Between Anti-CD40 MAb and Epstein-Barr Virus in Activation and Transformation of Human B Lymphocytes," *Human Antibodies*, 1997, pp. 43-47, vol. 8, No. 1.

Uckun, F.M. et al., "Temporal Association of CD40 Antigen Expression with Discrete Stages of Human B-Cell Ontogeny and the Efficacy of Anti-CD40 Immunotoxins Against Clonogenic B-Lineage Acute Lymphoblastic Leukemia as Well as B-Lineage Non-Hodgkin's Lymphoma Cells," *Blood*, 1990, pp. 2449-2459, vol. 76, No. 12.

Urakawa, T. et al., "Synthesis of Immunogenic, But Non-Infectious, Poliovirus Particles in Insect Cells by a Baculovirus Expression Vector," *J. gen. Virol.*, 1989, pp. 1453-1463, vol. 70.

Valle, A. et al., "mAb 104, A New Monoclonal Antibody, Recognizes the B7 Antigen that is Expressed on Activated B Cells and HTLV-1-Transformed T Cells," *Immunology*, 1990, pp. 531-535, vol. 69.

Ward, P.A. and M.S. Mulligan, "Blocking of Adhesion Molecules in vivo as Anti-Inflammatory Therapy," *Therapeutic Immunology*, 1994, pp. 165-171, vol. 1.

Webb, N. R. et al., Cell-Surface Expression and Purification of Human CD4 Produced in Baculovirus-Infected Insect Cells, *Proc. Natl. Acad. Sci.*, 1989, pp. 7731-7735, vol. 86, U.S.A.

Wetzel, G.D. et al., "Evidence for Two Distinct Activation States Available to B Lymphocytes," *Journal of Immunology*, 1984, pp. 2327-2332, vol. 135, No. 5.

Winter, G. and W.J. Harris, "Antibody-Based Therapy, Humanized Antibodies," *TIPS*, May 1993, pp. 139-143, vol. 14.

Yellin, M.J. et al., "CD40 Molecules Induce Down-Modulation and Endocytosis of T Cell Surface T Cell-B Cell Activating Molecule/CD4O-L," *J. of Immunology*, 1994, pp. 598-608, vol. 152.

Zhang, K. et al., "CD40 Stimulation Provides an IFN-y-Independent and IL-4 Dependent Differentiation Signal Directly to Human B Cells for IgE Production," *Journal of Immunology*, 1991, pp. 1836-1842, vol. 146, No. 6.

Zhou, Z-H et al., "An Agonist Anti-Human CD40 Monoclonal Antibody that Induces Dendritic Cell Formation and Maturation and Inhibits Proliferation of a Myeloma Cell Line," *Hybridoma*, 1999, pp. 471-478, vol. 18, No. 6.

METHODS OF THERAPY FOR B-CELL MALIGNANCIES USING ANTAGONIST ANTI-CD40 ANTIBODIES

CROSS REFERENCE TO RELATED APPLICATIONS

The present application is a continuation application of U.S. application Ser. No. 11/849,107, filed Aug. 31, 2007, now U.S. Pat. No. 7,445,780, which is a continuation application of U.S. application Ser. No. 10/380,223, filed Mar. 11, 2003, now U.S. Pat. No. 7,288,252, which is a National Stage of International Application No. PCT/US01/30963, filed Oct. 2, 2001, which claims the benefit of U.S. Provisional Application No. 60/237,556, filed Oct. 2, 2000, the contents of each of which are herein incorporated by reference in their entirety.

FIELD OF THE INVENTION

The present invention is directed to methods of therapy for diseases characterized by malignant B cells and tumors of B-cell origin using antagonist anti-CD40 antibodies or antigen-binding fragments thereof.

BACKGROUND OF THE INVENTION

B cells play an important role during the normal in vivo immune response. A foreign antigen will bind to surface immunoglobulins on specific B cells, triggering a chain of events including endocytosis, processing, presentation of processed peptides on MHC-class II molecules, and up-regulation of the B7 antigen on the B-cell surface. A specific T-cell then binds to the B cell via T-cell receptor (TCR) recognition of the processed antigen presented on the MHC-class II molecule. Stimulation through the TCR activates the T cell and initiates T-cell cytokine production. A second signal that further activates the T cell is an interaction between the CD28 antigen on T cells and the B7 antigen on B cells. When the above-mentioned signals are received, the CD40 ligand, which is not expressed on resting human T cells, is up-regulated on the T-cell surface. Binding of the CD40 ligand to the CD40 antigen on the B-cell surface stimulates the B cell, causing the B cell to mature into a plasma cell secreting high levels of soluble immunoglobulin.

CD40 is a cell-surface antigen present on the surface of both normal and neoplastic human B cells, dendritic cells, monocytic and epithelial cells, some epithelial carcinomas, and on antigen presenting cells (APCs). CD40 expression on APCs plays an important co-stimulatory role in the activation of both T helper and cytotoxic T lymphocytes. CD40 receptors are also found on eosinophils, synovial membranes in rheumatoid arthritis, activated platelets, inflamed vascular endothelial cells, dermal fibroblasts, and other non-lymphoid cell types. The CD40 receptor is expressed on activated T cells, activated platelets, and inflamed vascular smooth muscle cells. CD40 is also expressed at low levels on vascular endothelial cells and is up-regulated in areas of local inflammation.

Human CD40 is a peptide of 277 amino acids having a predicted molecular weight of 30,600, with a 19 amino acid secretory signal peptide comprising predominantly hydrophobic amino acids. The CD40 receptor exists in a highly modified glycoprotein state on the cell surface and migrates in sodium dodecyl sulfate (SDS)-polyacrylamide gels as an approximately 50 kDa polypeptide.

The CD40 antigen is known to be related to the human nerve growth factor (NGF) receptor, tumor necrosis factor-α (TNF-α) receptor, and Fas, suggesting that CD40 is a receptor for a ligand with important functions in B-cell activation. During B-cell differentiation, the molecule is first expressed on pre-B cells and then disappears from the cell surface when the B cell becomes a plasma cell. The CD40 cell-surface antigen plays an important role in B-cell proliferation and differentiation.

Binding of its ligand (termed CD40L or CD154) to the CD40 receptor stimulates B-cell proliferation and differentiation, antibody production, isotype switching, and B-cell memory generation. The human and murine CD40L (CD40 receptor) genes have been cloned (Spriggs et al. (1992) *J. Exp. Med.* 176:1543; Armitage et al. (1992) *Nature* 357:80; and U.S. Pat. No. 6,264,951). Engagement of CD40 receptors by the CD40 ligand on APCs, such as macrophages and dendritic cells, up-regulates cell-surface expression of MHC Class II and CD80/86, and induces the secretion of pro-inflammatory cytokines such as IL-8, IL-12, and TNF, all of which increase the potency of antigen presentation to T cells.

All B cells express common cell surface markers, including CD40. Transformed cells from patients with low- and high-grade B-cell lymphomas, B-cell acute lymphoblastic leukemia, multiple myeloma, chronic lymphocytic leukemia, and Hodgkin's disease express CD40. CD40 expression is also detected in two-thirds of acute myeloblastic leukemia cases and 50% of AIDS-related lymphomas. Further, malignant B cells from several tumors of B-cell lineage express a high degree of CD40 and appear to depend on CD40 signaling for survival and proliferation.

Additionally, immunoblastic B-cell lymphomas frequently arise in immunocompromised individuals such as allograft recipients and others receiving long-term immunosuppressive therapy, AIDS patients, and patients with primary immunodeficiency syndromes such as X-linked lymphoproliferative syndrome or Wiscott-Aldrich syndrome (Thomas et al. (1991) *Adv. Cancer Res.* 57:329; Straus et al. (1993) *Ann. Intern. Med.* 118:45). These tumors appear to arise as a result of impaired T-cell control of latent Epstein-Barr virus (EBV) infection. Similar lymphomas of human origin can be induced in mice with severe combined immunodeficiency syndrome (SCID) by inoculation of peripheral blood lymphocytes (PBL) from healthy, EBV-positive individuals (Mosier et al. (1988) *Nature* 335:256; Rowe et al (1991) *J. Exp. Med.* 173:147).

The pathogenesis of low-grade B-lineage malignancies, including non-Hodgkin's lymphoma and chronic lymphocytic leukemia, is strongly affected by the imbalance of the growth/survival signal by CD40 and a crippled death signal by Fas. Studies in low-grade non-Hodgkin's lymphoma suggest that the disease is the result of an accumulation of lymphomatous cells due to reduction in Fas-mediated apoptosis and an increase in the survival signal through CD40. CD40 provides a survival signal for lymphoma cells from non-Hodgkin's B-lymphoma patients and stimulates their growth in vitro (Romano et al. (2000) *Leuk. Lymphoma* 36:255-262; Furman et al. (2000) *J. Immunol.* 164:2200-2206; Kitada et al. (1999) *Br. J. Haematol.* 106:995-1004; Romano et al. (1998) *Blood* 92:990-995; Jacob et al. (1998) *Leuk. Res.* 22:379-382; Wang et al. (1997) *Br. J. Haematol.* 97:409-417; Planken et al. (1996) *Leukemia* 10:488-493; and Greiner et al. (1997) *Am J. Pathol.* 150:1583-1593).

Approximately 85% of non-Hodgkin's lymphomas, a diverse group of malignancies, are of B-cell origin. The non-Hodgkin's lymphomas originate from components of the spleen, thymus, and lymph nodes. In the Working Formulation classification scheme, these lymphomas been divided into low-, intermediate-, and high-grade categories by virtue of their natural histories (see "The Non-Hodgkin's Lymphoma Pathologic Classification Project," Cancer 49 (1982): 2112-2135). The low-grade or favorable lymphomas are indolent, with a median survival of 5 to 10 years (Horning and Rosenberg (1984) N. Engl. J. Med. 311:1471-1475). Although chemotherapy can induce remissions in the majority of indolent lymphomas, cures are rare, and most patients eventually relapse, requiring further therapy. The intermediate- and high-grade lymphomas are more aggressive tumors, but they have a greater chance for cure with chemotherapy. However, significant numbers of these patients will still relapse and require further treatment to induce remissions. Furthermore, patients undergoing chemotherapy can experience toxicity effects. Therefore, there is a need for new therapies for treating diseases of malignant B cells.

SUMMARY OF THE INVENTION

Methods for treating a patient with a disease comprising malignant B cells, including lymphomas such as, non-Hodgkin's lymphomas (high-grade lymphomas, intermediate-grade lymphomas, and low-grade lymphomas), Hodgkin's disease, acute lymphoblastic leukemias, myelomas, chronic lymphocytic leukemias, and myeloblastic leukemias are provided. The method comprises treating the patient with anti-CD40 antibodies or antigen-binding fragments thereof that are free of significant agonist activity when bound to a CD40 antigen on a normal human B cells and that exhibit antagonist activity when bound to a CD40 antigen on a malignant human B cell. Monoclonal antibodies and antigen-binding fragments thereof that are suitable for use in the methods of the invention exhibit the following characteristics: 1) are capable of specifically binding to a human CD40 antigen expressed on the surface of a human cell; 2) are free of significant agonist activity when bound to a CD40 antigen on a normal human B cell; and, 3) exhibit antagonist activity when bound to a CD40 antigen on a malignant human B cell. In some embodiments, the anti-CD40 antibody or fragment thereof also exhibits antagonist activity when bound to CD40 antigen on normal human B cells. The monoclonal antibodies have a strong affinity for CD40 and are characterized by a dissociation constant ($K_d$) of at least $10^{-5}$ M, preferably at least about $10^{-8}$ M to about $10^{-20}$ M, more preferably at least about $5 \times 10^{-9}$ to about $10^{-16}$ M. Suitable monoclonal antibodies have human constant regions; preferably they also have wholly or partially humanized framework regions; and most preferably are fully human antibodies or antigen-binding fragments thereof. Examples of such monoclonal antibodies are the antibody designated herein as 15B8, the monoclonal antibody produced by the hybridoma cell line designated 15B8, a monoclonal antibody comprising an amino acid sequence selected from the group consisting of SEQ ID NO:2 and SEQ ID NO:4; a monoclonal antibody comprising an amino acid sequence encoded by a nucleic acid molecule comprising a nucleotide sequence selected from the group consisting of SEQ ID NO:1 and SEQ ID NO:3; and antigen-binding fragments of these monoclonal antibodies that retain the capability of specifically binding to human CD40.

In one embodiment of the invention, the therapy comprises administering to a patient a therapeutically effective dose of a pharmaceutical composition comprising suitable anti-CD40 antibodies or antigen-binding fragments thereof. A therapeutically effective dose of the anti-CD40 antibody or fragment thereof is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the treatment may comprise administration of a single therapeutically effective dose or administration of multiple therapeutically effective doses of the anti-CD40 antibody or antigen-binding fragment thereof.

The anti-CD40 antibodies suitable for use in the methods of the invention may be modified. Modifications of the anti-CD40 antibodies include, but are not limited to, immunologically active chimeric anti-CD40 antibodies, humanized anti-CD40 antibodies, and immunologically active murine anti-CD40 antibodies.

DETAILED DESCRIPTION OF THE INVENTION

Figure 1:
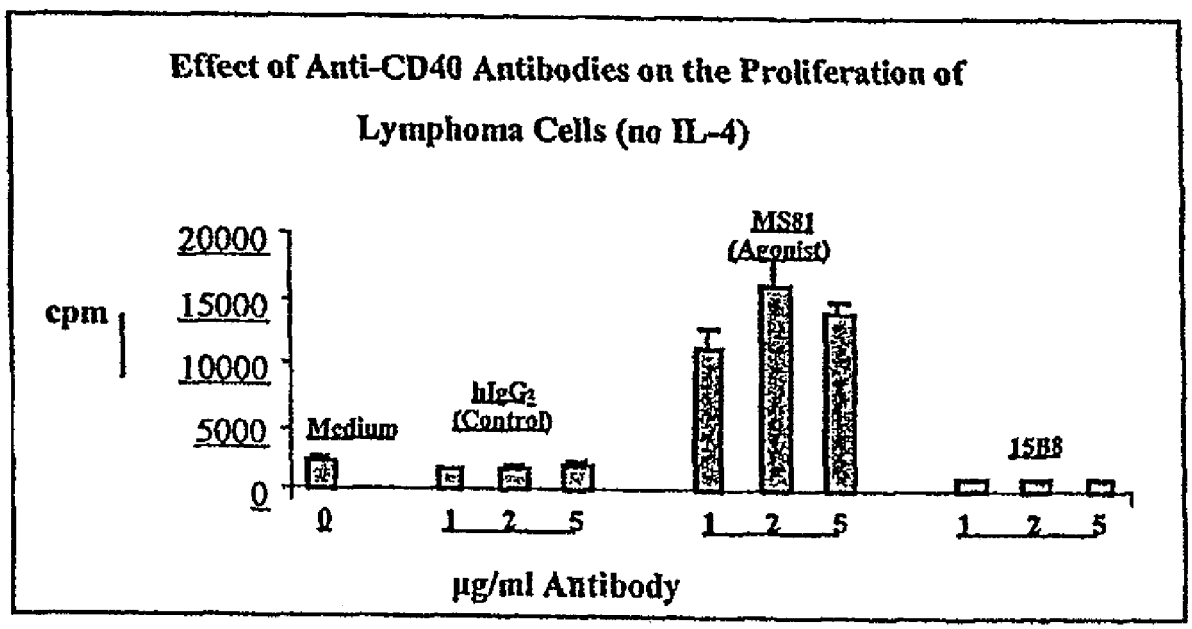
FIG. 1 depicts representative results of the effect of agonist (MS81) and antagonist (15B8) anti-CD40 antibodies at a concentration of 1, 2, or 5 µg/ml on the proliferation of non-Hodgkin's lymphoma (NHL) cells in vitro in the absence of interleukin-4 (IL-4). Malignant B cells were obtained from tumor infiltrated lymph nodes of a NHL patient. FACS analysis of the NHL cells confirmed that these cells expressed CD40 and bound the antagonist anti-CD40 antibody 15B8. See Example 3 below for details.

The present invention is directed to methods for treating human patients with diseases that originate from malignant B cells. The methods involve treatment with an anti-CD40 antibody or antigen-binding fragment thereof, where administration of the antibody or antigen-binding fragment thereof promotes a positive therapeutic response within the patient undergoing this method of therapy. Anti-CD40 antibodies suitable for use in the methods of the invention have the following characteristics: 1) they specifically bind a human CD40 antigen expressed on the surface of a human cell; 2) they are free of significant agonist activity when bound to a CD40 antigen on a normal human B cell; and 3) they exhibit antagonist activity when bound to a CD40 antigen on a malignant human B cell. These anti-CD40 antibodies and antigen-binding fragments thereof are referred to herein as antagonist anti-CD40 antibodies. Such antibodies include, but are not limited to, the fully human monoclonal antibody 15B8 described below and monoclonal antibodies having the binding characteristics of monoclonal antibody 15B8. As discussed in more detail below, these antibodies are specific to CD40 receptors. When these antibodies bind CD40 displayed on the surface of normal human B cells, the antibodies are free of significant agonist activity; in some embodiments, their binding to CD40 displayed on the surface of normal human B cells results in inhibition of proliferation and differentiation of these normal human B cells. Thus, the antagonist anti-CD40 antibodies suitable for use in the methods of the invention include those monoclonal antibodies that can exhibit antagonist activity toward normal human B cells expressing the cell-surface CD40 antigen. When antagonist anti-CD40 antibodies bind CD40 displayed on the surface of malignant human B cells, the antibodies exhibit antagonist activity as defined elsewhere herein.

"Treatment" is herein defined as the application or administration of an antagonist anti-CD40 antibody or antigen-binding fragment thereof to a patient, or application or administration of an antagonist anti-CD40 antibody or fragment thereof to an isolated tissue or cell line from a patient, where the patient has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. By "treatment" is also intended the application or administration of a pharmaceutical composition comprising the antagonist anti-CD40 antibodies or fragments thereof to a patient, or application or administration of a pharmaceutical composition comprising the anti-CD40 antibodies or fragments thereof to an isolated tissue or cell line from a patient, who has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

By "anti-tumor activity" is intended a reduction in the rate of malignant B-cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one anti-CD40 antibody (or antigen-binding fragment thereof) causes a physiological response that is beneficial with respect to treatment of disease states comprising malignant B cells in a human.

The monoclonal antibody 15B8 represents a suitable antagonist anti-CD40 antibody for use in the methods of the present invention. This antibody is described in U.S. Provisional Application Ser. No. 60/237,556, titled "Human Anti-CD40 Antibodies," filed Oct. 2, 2000, and PCT International Application No. PCT/US01/30857, also titled "Human Anti-CD40 Antibodies," filed Oct. 2, 2001 (Attorney Docket No. PP16092.003), both of which are herein incorporated by reference in their entirety. The 15B8 antibody is a fully human anti-CD40 monoclonal antibody of the $IgG_2$ isotype produced from the hybridoma cell line 15B8. The cell line was created using splenocytes from an immunized xenotypic mouse containing a human immunoglobulin locus (Abgenix). The spleen cells were fused with the mouse myeloma SP2/0 cells (Sierra BioSource). The resulting hybridomas were sub-cloned several times to create the stable monoclonal cell line 15B8. The hybridoma cell line 15B8 was deposited with the American Type Culture Collection (ATCC), 10801 University Boulevard, Manassas, Va., USA, on Oct. 25, 2001, under the terms of the Budapest Treaty and assigned Patent Deposit-Designation PTA-3814.

The 15B8 cell line was adapted to grow in protein-free medium and used to create a Master Cell Bank. The Master Cell Bank was tested for identity and adventitious and endogenous contaminants. The Master Cell Bank was used to manufacture the desired human $IgG_2$. The respective 15B8 antibody was purified using chromatography and filtration procedures.

The anti-CD40 antibody 15B8 is a polypeptide composed of 1,284 amino acid residues with a predicted molecular weight of 149,755 with two heavy chains and two light chains in a heterodimeric arrangement. Amino acid analysis reveals that the antibody is composed of equimolar amounts of heavy and light chains. The nucleotide and amino acid sequences for the variable region for the light chain are set forth in SEQ ID NO:1 and SEQ ID NO:2, respectively. The nucleotide and amino acid sequences for the variable region for the heavy chain are set forth in SEQ ID NO:3 and SEQ ID NO:4, respectively. The 15B8 monoclonal antibody binds soluble CD40 in ELISA-type assays. When tested in vitro for effects on proliferation of B cells from numerous primates, 15B8 acts as an agonistic anti-CD40 antibody in cynomologus, baboon, and rhesus monkeys. In assays with humans, chimpanzees, and marmosets, 15B8 is an antagonist anti-CD40 antibody. The binding affinity of 15B8 to human CD40 is $3.1 \times 10^{-9}$ M as determined by the Biacore™ assay.

Suitable antagonist anti-CD40 antibodies for use in the methods of the present invention exhibit a strong single-site binding affinity for the CD40 cell-surface antigen. The monoclonal antibodies of the invention exhibit a dissociation constant ($K_d$) for CD40 of at least $10^{-5}$ M, at least $3 \times 10^{-5}$ M, preferably at least $10^{-6}$ M to $10^{-7}$ M, more preferably at least $10^{-8}$ M to about $10^{-20}$ M, yet more preferably at least $5 \times 10^{-9}$ M to about $10^{-18}$ M, most preferably at least about $5 \times 10^{-9}$ M to about $10^{-16}$ M, such as $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, $10^{-15}$ M, $5 \times 10^{-16}$ M, or $10^{-16}$ M, as measured using a standard assay such as Biacore™. Biacore analysis is known in the art and details are provided in the "BIAapplications handbook."

By "CD40 antigen" is intended a glycosylated transmembrane peptide or any fragment thereof (GenBank Accession No. X60592; U.S. Pat. Nos. 5,674,492 and 4,708,871; Stamenkovic et al. (1989) *EMBO* 8:1403; Clark (1990) *Tissue Antigens* 36:33; Barclay et al. (1997) *The Leucocyte Antigen Facts Book* (2d ed.; Academic Press, San Diego)). The CD40 receptor is displayed on the surface of a variety of cell types, as described elsewhere herein. By "displayed on the surface" and "expressed on the surface" is intended that all or a portion of the CD40 antigen is exposed to the exterior of the cell. The displayed or expressed CD40 antigen may be fully or partially glycosylated.

By "agonist activity" is intended that the substance functions as an agonist. An agonist combines with a receptor on a cell and initiates a reaction or activity that is similar to or the same as that initiated by the receptor's natural ligand. An agonist of CD40 induces any or all of, but not limited to, the following responses: B-cell proliferation and differentiation, antibody production, intercellular adhesion, B-cell memory generation, isotype switching, up-regulation of cell-surface expression of MHC Class II and CD80/86, and secretion of pro-inflammatory cytokines such as IL-8, IL-12, and TNF. By "antagonist activity" is intended that the substance functions as an antagonist. An antagonist of CD40 prevents or reduces induction of any of the responses induced by binding of the CD40 receptor to an agonist ligand, particularly CD40L. The antagonist may reduce induction of any one or more of the responses to agonist binding by 5%, 10%, 15%, 20%, 25%, 30%, 35%, preferably 40%, 45%, 50%, 55%, 60%, more preferably 70%, 80%, 85%, and most preferably 90%, 95%, 99%, or 100%. Methods for measuring B-cell responses are known to one of skill in the art and include, but are not limited to, B-cell proliferation assays, Banchereau-Like-B-Cell proliferation assays, T-cell helper assays for antibody production, co-stimulation of B-cell proliferation assays, and assays for up-regulation of B-cell activation markers. Several of these assays are discussed in more detail elsewhere herein.

By "significant" agonist activity is intended an agonist activity of at least 30%, 35%, 40%, 45%, 50%, 60%, 70%, 75%, 80%, 85%, 90%, 95%, or 100% greater than the agonist activity induced by a neutral substance or negative control as measured in an assay of a B-cell response. A substance "free of significant agonist activity" would exhibit an agonist activity of not more than about 25% greater than the agonist activity induced by a neutral substance or negative control, preferably not more than about 20% greater, 15% greater, 10% greater, 5% greater, 1% greater, 0.5% greater, or even not more than about 0.1% greater than the agonist activity induced by a neutral substance or negative control as measured in an assay of a B-cell response. The antagonist anti-CD40 antibodies useful in the methods of the present invention are free of significant agonist activity as noted above when bound to a CD40 antigen on a normal human B cell. In one embodiment of the invention, the antagonist anti-CD40 antibody is free of significant agonist activity in one B-cell response. In another embodiment of the invention, the antagonist anti-CD40 antibody is free of significant agonist activity in assays of more than one B-cell response (e.g., proliferation and differentiation, or proliferation, differentiation, and antibody production).

As used herein "anti-CD40 antibody" encompasses any antibody that specifically recognizes the CD40 B-cell surface antigen, including polyclonal antibodies, monoclonal antibodies, single-chain antibodies, and fragments thereof such as Fab, F(ab')$_2$, F$_v$, and other fragments which retain the antigen binding function of the parent anti-CD40 antibody. Polyclonal sera may be prepared by conventional methods. In general, a solution containing the CD40 antigen is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies. Polyclonal sera can be prepared in a transgenic animal, preferably a mouse bearing human immunoglobulin loci. In a preferred embodiment, Sf9 cells expressing CD40 are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Preferably the antibody is monoclonal in nature. By "monoclonal antibody" is intended an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site, i.e., the CD40 B-cell surface antigen in the present invention. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

Monoclonal antibodies can be prepared using the method of Kohler et al (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

As an alternative to the use of hybridomas, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

Monoclonal antibodies to CD40 are known in the art. See, for example, the sections dedicated to B-cell antigen in McMichael, ed. (1987; 1989) *Leukocyte Typing III and IV* (Oxford University Press, New York); U.S. Pat. Nos. 5,674,492; 5,874,082; 5,677,165; 6,056,959; WO 00/63395; copending U.S. Provisional Patent Application Ser. No. 60/237,556, titled, "Human Anti-CD40 Antibodies," filed Oct. 2, 2000; Gordon et al. (1988) *J. Immunol.* 140:1425; Valle et al. (1989) *Eur. J. Immunol.* 19:1463; Clark et al. (1986) *PNAS* 83:4494; Paulie et al. (1989) *J. Immunol.* 142:590; Gordon et al. (1987) *Eur. J. Immunol.* 17:1535; Jabara et al. (1990) *J. Exp. Med.* 172:1861; Zhang et al. (1991) *J. Immunol.* 146:1836; Gascan et al. (1991) *J. Immunol.* 147:8; Banchereau et al. (1991) *Clin. Immunol. Spectrum* 3:8; and Banchereau et al. (1991) *Science* 251:70; all of which are herein incorporated by reference.

Additionally, the term "anti-CD40 antibody" as used herein encompasses chimeric anti-CD40 antibodies. By "chimeric" antibodies is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the CD40 cell-surface antigen. The non-human source can be any vertebrate source that can be used to generate antibodies to a human CD40 cell-surface antigen or material comprising a human CD40 cell-surface antigen. Such non-human sources include, but are not limited to, rodents (e.g., rabbit, rat, mouse, etc.; see, for example, U.S. Pat. No. 4,816,567, herein incorporated by reference) and non-human primates (e.g., Old World Monkey, Ape, etc.; see, for example, U.S. Pat. Nos. 5,750,105 and 5,756,096; herein incorporated by reference). As used herein, the phrase "immunologically active" when used in reference to chimeric anti-CD40 antibodies means a chimeric antibody that binds human CD40.

Humanized anti-CD40 antibodies are also encompassed by the term anti-CD40 antibody as used herein. By "humanized" is intended forms of anti-CD40 antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) *Nature* 331:522-525; Riechmann et al. (1988) *Nature* 332:323-329; and Presta (1992) *Curr. Op. Struct. Biol.* 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

Also encompassed by the term anti-CD40 antibodies are xenogeneic or modified anti-CD40 antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598, herein incorporated by reference.

Fragments of the anti-CD40 antibodies are suitable for use in the methods of the invention so long as they retain the desired affinity of the full-length antibody. Thus, a fragment of an anti-CD40 antibody will retain the ability to bind to the CD40 B-cell surface antigen. Such fragments are characterized by properties similar to the corresponding full-length antagonist anti-CD40 antibody, that is the fragments will 1) specifically bind a human CD40 antigen expressed on the surface of a human cell; 2) are free of significant agonist activity when bound to a CD40 antigen on a normal human B cell; and 3) exhibit antagonist activity when bound to a CD40 antigen on a malignant human B cell. Where the full-length antagonist anti-CD40 antibody exhibits antagonist activity when bound to the CD40 antigen on the surface of a normal human B cell, the fragment will also exhibit such antagonist activity. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778; 5,260,203; 5,455,030; 5,856,456; herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, New York), pp. 269-315.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

Antagonist anti-CD40 antibodies useful in the methods of the present invention include the 15B8 monoclonal antibody disclosed herein as well as antibodies differing from this antibody but retaining the CDRs; and antibodies with one or more amino acid addition(s), deletion(s), or substitution(s), wherein the antagonist activity is measured by inhibition of malignant B cell proliferation and/or differentiation. The invention also encompasses de-immunized antagonist anti-CD40 antibodies, which can be produced as described in, for example, International Publication Nos. WO 98/52976 and WO 0034317; herein incorporated by reference. In this manner, residues within the antagonist anti-CD40 antibodies of the invention are modified so as to render the antibodies non- or less immunogenic to humans while retaining their antagonist activity toward malignant human B cells, wherein such activity is measured by assays noted elsewhere herein. Also included within the scope of the claims are fusion proteins comprising an antagonist anti-CD40 antibody of the invention, or a fragment thereof, which fusion proteins can be synthesized or expressed from corresponding polynucleotide vectors, as is known in the art. Such fusion proteins are described with reference to conjugation of antibodies as noted below.

The antibodies of the present invention can have sequence variations produced using methods described in, for example, Patent Publication Nos. EP 0 983 303 A1, WO 00/34317, and WO 98/52976, incorporated herein by reference. For example, it has been shown that sequences within the CDR can cause an antibody to bind to MHC Class II and trigger an unwanted helper T cell response. A conservative substitution can allow the antibody to retain binding activity yet lose its ability to trigger an unwanted T cell response. Any such conservative or non-conservative substitutions can be made using art-recognized methods, such as those noted elsewhere herein, and the resulting antibodies will fall within the scope of the invention. The variant antibodies can be routinely tested for antagonist activity, affinity, and specificity using methods described herein.

An antibody produced by any of the methods described above, or any other method not disclosed herein, will fall within the scope of the invention if it possesses at least one of the following biological activities: inhibition of immunoglobulin secretion by normal human peripheral B cells stimulated by T cells; inhibition of proliferation of normal human peripheral B cells stimulated by Jurkat T cells; inhibition of proliferation of normal human peripheral B cells stimulated by CD40L-expressing cells; and inhibition of proliferation of human malignant B cells as noted below. These assays can be performed as described in the Examples herein. See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

Any of the previously described antagonist anti-CD40 antibodies or antibody fragments thereof may be conjugated prior to use in the methods of the present invention. Methods for producing conjugated antibodies are known in the art. Thus, the anti-CD40 antibody may be labeled using an indirect labeling or indirect labeling approach. By "indirect labeling" or "indirect labeling approach" is intended that a chelating agent is covalently attached to an antibody and at least one radionuclide is inserted into the chelating agent. See, for example, the chelating agents and radionuclides described in Srivagtava and Mease (1991) *Nucl. Med. Bio.* 18:589-603, herein incorporated by reference. Alternatively, the anti-CD40 antibody may be labeled using "direct labeling" or a "direct labeling approach", where a radionuclide is covalently attached directly to an antibody (typically via an amino acid residue). Preferred radionuclides are provided in Srivagtava and Mease (1991) supra. The indirect labeling approach is particularly preferred. See also, for example, International Publication Nos. WO 00/52031 and WO 00/52473, where a linker is used to attach a radioactive label to antibodies; and the labeled forms of anti-CD40 antibodies described in U.S. Pat. No. 6,015,542; herein incorporated by reference.

Further, an antibody (or fragment thereof) may be conjugated to a therapeutic moiety such as a cytotoxin, a therapeutic agent, or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, interferon-alpha, interferon-beta, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known. See, for example, Arnon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-256; ed. Hellstrom et al. (1987) "Antibodies for Drug Delivery," in *Controlled Drug Delivery*, ed. Robinson et al. (2d ed; Marcel Dekker, Inc.), pp. 623-653; Thorpe (1985) "Antibody Carriers of Cytotoxic Agents in Cancer Therapy: A Review," in *Monoclonal Antibodies '84: Biological and Clinical Applications*, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in *Monoclonal Antibodies for Cancer Detection and Therapy*, ed. Baldwin et al. (Academic Press, New York, 1985), pp. 303-316; and Thorpe et al. (1982) *Immunol. Rev.* 62:119-158.

Alternatively, an antibody can be conjugated to a second antibody to form an antibody heteroconjugate as described by Segal in U.S. Pat. No. 4,676,980. In addition, linkers may be used between the labels and the antibodies of the invention (see U.S. Pat. No. 4,831,175). Antibodies or, antigen-binding fragments thereof may be directly labeled with radioactive iodine, indium, yttrium, or other radioactive particle known in the art (U.S. Pat. No. 5,595,721). Treatment may consist of a combination of treatment with conjugated and nonconjugated antibodies administered simultaneously or subsequently (WO 00/52031 and WO 00/52473).

Methods of the invention are directed to the use of antagonist anti-CD40 antibodies to treat patients having a disease comprising malignant B cells. By "malignant" B cell is intended any neoplastic B cell, including but not limited to B cells derived from lymphomas including low-, intermediate-, and high-grade B-cell lymphomas, immunoblastic lymphomas, non-Hodgkin's lymphomas, Hodgkin's disease, Epstein-Barr Virus (EBV) induced lymphomas, and AIDS-related lymphomas, as well as B-cell acute lymphoblastic leukemias, myelomas, chronic lymphocytic leukemias, acute myeloblastic leukemias, and the like.

The methods of the invention find use in the treatment of non-Hodgkin's lymphomas related to abnormal, uncontrollable B cell proliferation or accumulation. For purposes of the present invention, such lymphomas will be referred to according to the Working Formulation classification scheme, that is those B-cell lymphomas categorized as low grade, intermediate grade, and high grade (see "The Non-Hodgkin's Lymphoma Pathologic Classification Project," *Cancer* 49(1982): 2112-2135). Thus, low-grade B-cell lymphomas include small lymphocytic, follicular small-cleaved cell, and follicular mixed small-cleaved and large cell lymphomas; intermediate-grade lymphomas include follicular large cell, diffuse small cleaved cell, diffuse mixed small and large cell, and diffuse large cell lymphomas; and high-grade lymphomas include large cell immunoblastic, lymphoblastic, and small non-cleaved cell lymphomas of the Burkitt's and non-Burkitt's type.

It is recognized that the methods of the invention are useful in the therapeutic treatment of B-cell lymphomas that are classified according to the Revised European and American Lymphoma Classification (REAL) system. Such B-cell lymphomas include, but are not limited to, lymphomas classified as precursor B-cell neoplasms, such as B-lymphoblastic leukemia/lymphoma; peripheral B-cell neoplasms, including B-cell chronic lymphocytic leukemia/small lymphocytic lymphoma, lymphoplasmacytoid lymphoma/immunocytoma, mantle cell lymphoma (MCL), follicle center lymphoma (follicular) (including diffuse small cell, diffuse mixed small and large cell, and diffuse large cell lymphomas), marginal zone B-cell lymphoma (including extranodal, nodal, and splenic types), hairy cell leukemia, plasmacytoma/myeloma, diffuse large cell B-cell lymphoma of the subtype primary mediastinal (thymic), Burkitt's lymphoma, and Burkitt's like high grade B-cell lymphoma; acute leukemias; acute lymphocytic leukemias; myeloblastic leukemias; acute myelocytic leukemias; promyelocytic leukemia; myelomonocytic leukemia; monocytic leukemia; erythroleukemia; granulocytic leukemia (chronic myelocytic leukemia); chronic lymphocytic leukemia; polycythemia vera; multiple myeloma; Waldenstrom's macroglobulinemia; heavy chain disease; and unclassifiable low-grade or high-grade B-cell lymphomas.

It is recognized that the methods of the invention may be useful in preventing further tumor outgrowths arising during therapy. The methods of the invention are particularly useful in the treatment of subjects having low-grade B-cell lymphomas, particularly those subjects having relapses following standard chemotherapy. Low-grade B-cell lymphomas are more indolent than the intermediate- and high-grade B-cell lymphomas and are characterized by a relapsing/remitting course. Thus, treatment of these lymphomas is improved using the methods of the invention, as relapse episodes are reduced in number and severity.

The antagonist anti-CD40 antibodies described herein may also find use in the treatment of inflammatory diseases and deficiencies or disorders of the immune system including, but not limited to, systemic lupus erythematosus, psoriasis, scleroderma, CREST syndrome, inflammatory myositis, Sjogren's syndrome, mixed connective tissue disease, rheumatoid arthritis, multiple sclerosis, inflammatory bowel disease, acute respiratory distress syndrome, pulmonary inflammation, idiopathic pulmonary fibrosis, osteoporosis, delayed type hypersensitivity, asthma, primary biliary cirrhosis, and idiopathic thrombocytopenic purpura.

In accordance with the methods of the present invention, at least one antagonist anti-CD40 antibody (or antigen-binding fragment thereof) as defined elsewhere herein is used to promote a positive therapeutic response with respect to a malignant human B cell. By "positive therapeutic response" is intended an improvement in the disease in association with the anti-tumor activity of these antibodies or fragments thereof, and/or an improvement in the symptoms associated with the disease. That is, an anti-proliferative effect, the prevention of further tumor outgrowths, and/or a decrease in B symptoms can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only. In addition to these positive therapeutic responses, the subject undergoing therapy with the antagonist anti-CD40 antibody or antigen-binding fragment thereof may experience the beneficial effect of an improvement in the symptoms associated with the disease. Thus the subject may experience a decrease in the so-called B symptoms, i.e., night sweats, fever, weight loss, and/or urticaria.

By "therapeutically effective dose or amount" is intended an amount of antagonist anti-CD40 antibody or antigen-binding fragment thereof that, when administered brings about a positive therapeutic response with respect to treatment of a patient with a disease comprising malignant B cells. Administration of the pharmaceutical composition comprising the therapeutically effective dose or amount can be achieved using any acceptable administration method known in the art. Preferably the pharmaceutical composition comprising the antagonist anti-CD40 antibody or antigen-binding fragment thereof is administered intravenously, preferably by infusion over a period of about 1 to about 10 hours, more preferably over about 1 to about 8 hours, even more preferably over about 2 to about 7 hours, still more preferably over about 4 to about 6 hours, depending upon the anti-CD40 antibody being administered. The initial infusion with the pharmaceutical composition may be given over a period of about 4 to about 6 hours with subsequent infusions delivered more quickly. Subsequent infusions may be administered over a period of about 1 to about 6 hours, preferably about 1 to about 4 hours, more preferably about 1 to about 3 hours, yet more preferably about 1 to about 2 hours.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The anti-CD40 antibodies are typically provided by standard technique within a pharmaceutically acceptable buffer, for example, sterile saline, sterile buffered water, propylene glycol, combinations of the foregoing, etc. Methods for preparing parenterally administrable agents are described in *Remington's Pharmaceutical Sciences* (18$^{th}$ ed.; Mack Publishing Company, Eaton, Pa., 1990), herein incorporated by reference. See also, for example, WO 98/56418, which describes stabilized antibody pharmaceutical formulations suitable for use in the methods of the present invention.

The amount of at least one anti-CD40 antibody or fragment thereof to be administered is readily determined by one of ordinary skill in the art without undue experimentation. Factors influencing the mode of administration and the respective amount of at least one antagonist anti-CD40 antibody (or fragment thereof) include, but are not limited to, the particular lymphoma undergoing therapy, the severity of the disease, the history of the disease, and the age, height, weight, health, and physical condition of the individual undergoing therapy. Similarly, the amount of antagonist anti-CD40 antibody or fragment thereof to be administered will be dependent upon the mode of administration and whether the subject will undergo a single dose or multiple doses of this anti-tumor agent. Generally, a higher dosage of anti-CD40 antibody or fragment thereof is preferred with increasing weight of the patient undergoing therapy. The dose of anti-CD40 antibody or fragment thereof to be administered is in the range from about 0.003 mg/kg to about 50 mg/kg, preferably in the range of 0.01 mg/kg to about 40 mg/kg. Thus, for example, the dose can be 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, or 50 mg/kg.

In another embodiment of the invention, the method comprises administration of multiple doses of antagonist anti-CD40 antibody or fragment thereof. The method may comprise administration of 1, 2, 3, 4, 5, 6, 7, 8, 9, 10, 15, 20, 25, 30, 35, 40, or more therapeutically effective doses of a pharmaceutical composition comprising an antagonist anti-CD40 antibody or fragment thereof. The frequency and duration of administration of multiple doses of the pharmaceutical compositions comprising anti-CD40 antibody or fragment thereof can be readily determined by one of skill in the art without undue experimentation. Moreover, treatment of a subject with a therapeutically effective amount of an antibody can include a single treatment or, preferably, can include a series of treatments. In a preferred example, a subject is treated with antagonist anti-CD40 antibody or antigen-binding fragment thereof in the range of between about 0.1 to 20 mg/kg body weight, once per week for between about 1 to 10 weeks, preferably between about 2 to 8 weeks, more preferably between about 3 to 7 weeks, and even more preferably for about 4, 5, or 6 weeks. Treatment may occur annually to prevent relapse or upon indication of relapse. It will also be appreciated that the effective dosage of antibody or antigen-binding fragment thereof used for treatment may increase or decrease over the course of a particular treatment. Changes in dosage may result and become apparent from the results of diagnostic assays as described herein. Thus, in one embodiment, the dosing regimen includes a first administration of a therapeutically effective dose of at least one anti-CD40 antibody or fragment thereof on days 1, 7, 14, and 21 of a treatment period. In another embodiment, the dosing regimen includes a first administration of a therapeutically effective dose of at least one anti-CD40 antibody or fragment thereof on days 1, 2, 3, 4, 5, 6, and 7 of a week in a treatment period. Further embodiments include a dosing regimen having a first administration of a therapeutically effective dose of at least one anti-CD40 antibody or fragment thereof on days 1, 3, 5, and 7 of a week in a treatment period; a dosing regimen including a first administration of a therapeutically effective dose of at least one anti-CD40 antibody or fragment thereof on days 1 and 3 of a week in a treatment period; and a preferred dosing regimen including a first administration of a therapeutically effective dose of at least one anti-CD40 antibody or fragment thereof on day 1 of a week in a treatment period. The treatment period may comprise 1 week, 2 weeks, 3 weeks, a month, 3 months, 6 months, or a year. Treatment periods may be subsequent or separated from each other by a day, a week, 2 weeks, a month, 3 months, 6 months, or a year.

The antagonist anti-CD40 antibodies present in the pharmaceutical compositions described herein for use in the methods of the invention may be native or obtained by recombinant techniques, and may be from any source, including mammalian sources such as, e.g., mouse, rat, rabbit, primate, pig, and human. Preferably such polypeptides are derived from a human source, and more preferably are recombinant, human proteins from hybridoma cell lines.

The pharmaceutical compositions useful in the methods of the invention may comprise biologically active variants of the antagonist anti-CD40 antibodies of the invention. Such variants should retain the desired biological activity of the native polypeptide such that the pharmaceutical composition comprising the variant polypeptide has the same therapeutic effect as the pharmaceutical composition comprising the native polypeptide when administered to a subject. That is, the variant anti-CD40 antibody will serve as a therapeutically active component in the pharmaceutical composition in a manner similar to that observed for the native antagonist antibody, for example 15B8 as expressed by the hybridoma cell line 15B8. Methods are available in the art for determining whether a variant anti-CD40 antibody retains the desired biological activity, and hence serves as a therapeutically active component in the pharmaceutical composition. Biological activity of antibody variants can be measured using assays specifically designed for measuring activity of the native antagonist antibody, including assays described in the present invention.

Suitable biologically active variants of native or naturally occurring antagonist anti-CD40 antibodies can be fragments, analogues, and derivatives of that polypeptide. By "fragment" is intended a polypeptide consisting of only a part of the intact polypeptide sequence and structure, as noted elsewhere herein. By "analogue" is intended an analogue of either the native polypeptide or of a fragment of the native polypeptide, where the analogue comprises a native polypeptide sequence and structure having one or more amino acid substitutions, insertions, or deletions. By "derivative" is intended any suitable modification of the native polypeptide of interest, of a fragment of the native polypeptide, or of their respective analogues, such as glycosylation, phosphorylation, polymer conjugation (such as with polyethylene glycol), or other addition of foreign moieties, so long as the desired biological activity of the native polypeptide is retained. Methods for making polypeptide fragments, analogues, and derivatives are generally available in the art.

For example, amino acid sequence variants of an antagonist anti-CD40 antibody can be prepared by mutations in the cloned DNA sequence encoding the antibody of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the antagonist anti-CD40 antibody polypeptide of interest, modifications are made such that variants continue to possess the desired activity, i.e., similar binding affinity and having the following characteristics: 1) are capable of specifically binding to a human CD40 antigen expressed on the surface of a human cell; 2) are free of significant agonist activity when bound to a CD40 antigen on a normal human B cell; and, 3) exhibit antagonist activity when bound to a CD40 antigen on a malignant human B cell. Obviously, any mutations made in the DNA encoding the variant polypeptide must not place the sequence out of reading frame and preferably will not create complementary regions that could produce secondary mRNA structure. See EP Patent Application Publication No. 75,444.

Biologically active variants of anti-CD40 antibodies will generally have at least 70%, preferably at least 80%, more preferably about 90% to 95% or more, and most preferably about 98% or more amino acid sequence identity to the amino acid sequence of the reference polypeptide molecule, which serves as the basis for comparison. A biologically active variant of a reference antagonist anti-CD40 antibody having the specificity and binding characteristics described herein may differ from the reference polypeptide by as few as 1-15 amino acids, as few as 1-10, such as 6-10, as few as 5, as few as 4, 3, 2, or even 1 amino acid residue. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule. The percentage sequence identity between two amino acid sequences is calculated by determining the number of positions at which the identical amino acid residue occurs in both sequences to yield the number of matched positions, dividing the number of matched positions by the total number of positions in the segment undergoing comparison to the reference molecule, and multiplying the result by 100 to yield the percentage of sequence identity.

For purposes of optimal alignment of the two sequences, the contiguous segment of the amino acid sequence of the variants may have additional amino acid residues or deleted amino acid residues with respect to the amino acid sequence of the reference molecule. The contiguous segment used for comparison to the reference amino acid sequence will comprise at least twenty (20) contiguous amino acid residues, and may be 30, 40, 50, 100, or more residues. Corrections for increased sequence identity associated with inclusion of gaps in the variant's amino acid sequence can be made by assigning gap penalties. Methods of sequence alignment are well known in the art for both amino acid sequences and for the nucleotide sequences encoding amino acid sequences.

Thus, the determination of percent identity between any two sequences can be accomplished using a mathematical algorithm. One preferred, non-limiting example of a mathematical algorithm utilized for the comparison of sequences is the algorithm of Myers and Miller (1988) *CABIOS* 4:11-17.

Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See the website at ncbi.nlm.nih.gov. Also see the ALIGN program (Dayhoff (1978) in *Atlas of Protein Sequence and Structure* 5:Suppl. 3 (National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Computer Applic. Biol. Sci.* 4:11-17.

The precise chemical structure of a polypeptide capable of specifically binding CD40 and retaining antagonist activity, particularly when bound to CD40 antigen on malignant B cells, depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of antagonist anti-CD40 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-CD40 antibody used herein so long as the antagonist properties of the anti-CD40 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy antagonist activity do not remove the polypeptide sequence from the definition of anti-CD40 antibodies of interest as used herein.

The art provides substantial guidance regarding the preparation and use of polypeptide variants. In preparing the anti-CD40 antibody variants, one of skill in the art can readily determine which modifications to the native protein nucleotide or amino acid sequence will result in a variant that is suitable for use as a therapeutically active component of a pharmaceutical composition used in the methods of the present invention.

Any pharmaceutical composition comprising an antagonist anti-CD40 antibody as the therapeutically active component can be used in the methods of the invention. Thus liquid, lyophilized, or spray-dried compositions comprising antagonist anti-CD40 antibodies or variants thereof that are known in the art may be prepared as an aqueous or nonaqueous solution or suspension for subsequent administration to a subject in accordance with the methods of the invention. Each of these compositions will comprise anti-CD40 antibodies or variants thereof as a therapeutically or prophylactically active component. By "therapeutically or prophylactically active component" is intended the anti-CD40 antibody or variant thereof is specifically incorporated into the composition to bring about a desired therapeutic or prophylactic response with regard to treatment, prevention, or diagnosis of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

Formulants may be added to pharmaceutical compositions comprising an anti-CD40 antibody of the invention. These formulants may include, but are not limited to, oils, polymers, vitamins, carbohydrates, amine acids, salts, buffers, albumin, surfactants, or bulking agents. Preferably carbohydrates include sugar or sugar alcohols such as mono-, di-, or polysaccharides, or water soluble glucans. The saccharides or glucans can include fructose, glucose, mannose, sorbose, xylose, maltose, sucrose, dextran, pullulan, dextrin, $\alpha$ and $\beta$ cyclodextrin, soluble starch, hydroxyethyl starch, and carboxymethylcellulose, or mixtures thereof. "Sugar alcohol" is defined as a $C_4$ to $C_8$ hydrocarbon having a hydroxyl group and includes galactitol, inositol, mannitol, xylitol, sorbitol, glycerol, and arabitol. These sugars or sugar alcohols may be used individually or in combination. The sugar or sugar alcohol concentration is between 1.0% and 7% w/v., more preferably between 2.0% and 6.0% w/v. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. Surfactants that can be added to the formulation are shown in EP Nos. 270,799 and 268,110.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546; which are all hereby incorporated by reference in their entireties. Preferred polymers are polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1,000 and 40,000, more preferably between 2,000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG The structure for POG is shown in Knauf et al. (1988) *J. Bio. Chem.* 263:15064-15070, and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al. (1982) *Cancer Research* 42:4734; Cafiso (1981) *Biochem Biophys Acta* 649:129; and Szoka (1980) *Ann. Rev. Biophys. Eng.* 9:467. Other drug delivery systems are known in the art and are described in, e.g., Poznansky et al. (1980) *Drug Delivery Systems* (R. L. Juliano, ed., Oxford, N.Y.) pp. 253-315; Poznansky (1984) *Pharm Revs* 36:277.

A further embodiment of the invention is the use of antagonist anti-CD40 antibodies for diagnostic monitoring of protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

The antagonist anti-CD40 antibodies can be used in combination with known chemotherapeutics and cytokines for the treatment of disease states comprising malignant B cells. For example, the anti-CD40 antibodies of the invention can be used in combination with cytokines such as interleukin-2. In another embodiment, the anti-CD40 antibodies of the invention can be used in combination with Rituximab (IDEC-C2B8; Rituxan®; IDEC Pharmaceuticals Corp., San Diego, Calif.). Rituximab is a chimeric anti-CD20 monoclonal antibody containing human IgG1 and kappa constant regions with murine variable regions isolated from a murine anti-CD20 monoclonal antibody, IDEC-2B8 (Reff et al. (1994) *Blood* 83:435-445).

The anti-CD40 antibodies described herein can further be used to provide reagents, e.g., labeled or labelable antibodies that can be used, for example, to identify cells expressing CD40. This can be very useful in determining the cell type of an unknown sample. Panels of monoclonal antibodies can be used to identify tissue by species and/or by organ type. In a similar fashion, these anti-CD40 antibodies can be used to screen tissue culture cells for contamination (i.e., screen for the presence of a mixture of CD40-expressing and non-CD40 expressing cells in a culture).

The following examples are offered by way of illustration and not by way of limitation.

EXPERIMENTAL

The antagonist anti-CD40 antibody used in the examples below is 15B8. 15B8 is a human $IgG_2$ subtype anti-human CD40 monoclonal antibody generated by immunization of transgenic mice bearing the human IgG2 heavy chain locus and the human K light chain locus (Xenomouse®, Abgenix). As shown by FACS analysis, 15B8 binds specifically to human CD40 and cross-reacts with CD40 expressed on the peripheral blood B cells from monkeys (cynomologus, rhesus and baboons) and chimpanzees. 15B8 does not cross-react with CD40 from non-primate animal species, nor does it bind to other members of the TNF receptor family as demonstrated by ELISA and FACS analysis. The binding affinity of 15B8 to human CD40 is $3.1 \times 10^{-9}M$ as determined by Biacore™ assay.

Example 1

Effect of 15B8 on the CD40/CD40L Interaction In Vitro

A competitive binding assay was performed to determine if direct competition for CD40 binding is a mechanism of the antagonist activity of 15B8.

A line of Chinese Hamster Ovary (CHO) cells containing the gene encoding CD40L and expressing CD40L on the cell surface was generated. The CD40L-expressing CHO cells were incubated with purified CD40 before and after incubation of CD40 with 15B8. Fluorescein isothiocyanate (FITC)-labeled anti-huIgG was added to the cells. FACS analysis was performed to detect 15B8 bound to the CHO cells via CD40. The binding of 15B8 to CD40 inhibited the subsequent binding of CD40L to CD40. However, when CD40L and CD40 were incubated together prior to the addition of 15B8, 15B8 was subsequently able to bind CD40. While not bound by any mechanism of action, this suggests that 15B8 does not compete directly with CD40L for binding sites on CD40, and that the binding of 15B8 to CD40 possibly caused conformational changes in the CD40 molecule that prevented the binding of CD40L to CD40. The putative structural alteration of the CD40 molecule induced by 15B8 binding could also deliver a negative signal to the cell causing the antagonist effect.

Example 2

Pharmacologic Action of 15B8 in Lymphoma Cells from NHL Patients

To demonstrate the potential efficacy of 15B8 in a preclinical in vitro model of non-Hodgkin's lymphoma (NHL), 15B8 was tested using malignant B cells (NHL cells) obtained from NHL patients who were either Rituximab-treated or naïve. Rituximab (IDEC-C2B8; Rituxan®; IDEC Pharmaceuticals Corp., San Diego, Calif.) is an anti-CD20 monoclonal antibody for the treatment of relapsed or refractory low-grade or follicular NHL.

Since primary lymphoma cells do not proliferate in regular culture medium and undergo apoptosis after a few days in culture, tumor cells were co-cultured with irradiated CD40-ligand (CD40L) transfected feeder cells (Arpin et al. (1995) *Science* 268:720-722) in the presence or absence of the B-cell growth factor interleukin-4 (IL-4). Antibodies (agonist anti-CD40 MS81, antagonist anti-CD40 15B8, or isotype control human IgG2 (huIgG2)) of indicated concentration (from 0.01 µg/ml to 10 µg/ml) were then added to the culture. Following incubation at 37° C. for 48 hours, cultured cells were pulsed with $^3$H-thymidine for 18 hours. The cells were then harvested and analyzed for the amount of $^3$H-thymidine incorporation (Schultze et al. (1995) *Proc. Natl. Acad. Sci. USA* 92:8200-8204). All sample conditions were in triplicate.

In these NHL cell primary culture assays, 15B8 alone or in combination with IL-4 did not stimulate NHL cells to proliferate in vitro. In contrast, an agonist anti-CD40 MS81 induced NHL cell proliferation under the same conditions. 15B8 showed statistically significant inhibition of NHL cell proliferation stimulated by CD40L (P=0.05) and by CD40L plus IL-4 (P<0.05) in vitro. At 1-10 µg/ml or 0.1-10 µg/ml concentration range respectively, 15B8 showed a statistically significant dose-related inhibition of NHL cell-proliferation stimulated by CD40L or by CD40L plus IL-4 (P<0.005) (data not shown).

There are two types of preclinical models that are currently used for evaluation of human antigen-specific monoclonal antibodies (Mabs) in therapeutic development for lymphomas. One model is the xenograft mouse in vivo model, where the EBV-transformed lymphoma cell lines, such as Daudi (Burkitt lymphoma) or Raji (Burkitt lymphoma) cells, are xenografted into SCID/Nude mice. The defects of these models are that the results only reflect effects on the particular immortal cell line, which is derived from one EBV-transformed cell. It is known that Burkitt lymphoma cells are lymphoblastoid cells (Ambinder et al. (1999) *Cancer Treat. Res.* 99:27-45; Quintanilla-Martinez et al. (1998) *Leuk. Lymphoma* 30:111-121; Klein (1996) *Acta Microbiol. Immunol. Hung.* 43:97-105) while the lymphoma cells from NHL patients are believed to be at the mature B cell stage (Ghia et al. (2000) *Adv. Cancer Res.* 79:157-173). EBV transformation of B cells results in changes of many components in the CD40 signaling pathway (Uchida et al. (1999) *Science* 286: 300-303; Farrell et al. (1997) *Biomed. Pharmacother.* 51:258-267). In contrast to CD40 signaling in NHL cells and normal B cells, CD40 signaling leads to growth arrest in EBV-transformed Burkitt lymphoma cell lines (Fukuda et al. (2000) *Viral Immunol.* 13:215-229; Baker et al. (1998) *Blood* 92:2830-2843). Thus, the results of testing an antagonist anti-CD40 MAb (15B8) in the xenograft models will not be able to predict the response to the antibody (15B8) by NHL patients.

The other model is the in vitro growth inhibition assay of lymphoma cells from NHL patients, which was used above. The advantage is that the results predicate the sensitivity of the lymphoma cells from NHL patients to the agent (15B8) tested. However, the results are obtained from in vitro study under defined conditions. A previous published study reported that a rat anti-mouse CD40, which failed to induce ADCC and CDC in vitro, showed good efficacy in two syngeneic mouse B lymphoma models (BCL1 and A31) (Tutt et al. (1998) *J. Immunol.* 161:3176-3185). The anti-tumor effect of the anti-mouse CD40 occurred slower in time than an anti-Id tested. One of the hypotheses was that the anti-mouse CD40 operated by blocking critical growth signals that are dependent on the expression of surface CD40, not direct signaling like anti-Id in the mouse models tested. When tested, 15B8 did not bind to the Fcγ receptors in vitro and failed to induce ADCC and CDC in vitro (data not shown) since it is of human IgG2 subtype. 15B8 has similar properties to the rat anti-mouse CD40. These data support the hypothesis that 15B8 will be beneficial to NHL patients, especially Rituxan™-resistant patients.

Example 3

Effect of 15B8 on Malignant B-Cell Proliferation In Vitro

To test if 15B8 provides the growth signal like CD40L in vitro, B cells from tumor infiltrated lymph nodes (NHL cells) were obtained from one antibody naïve, one Rituximab-sensitive and one Rituximab-resistant NHL patient. The NHL cells were studied under four different culture conditions: no added antibody (medium); addition of human isotype antibody IgG2 (control; referred to as huIgG2); addition of anti-CD40 antibody MS81 (agonistic antibody); and addition of 15B8. All antibodies were tested at 1, 2, and 5 µg/ml in the presence or absence of IL-4. The NHL cells from two patients were cultured as described above under the same four conditions in the presence of IL-4 (2 ng/ml). B-cell proliferation was measured by $^3$H-thymidine incorporation as described above.

Figure 2:
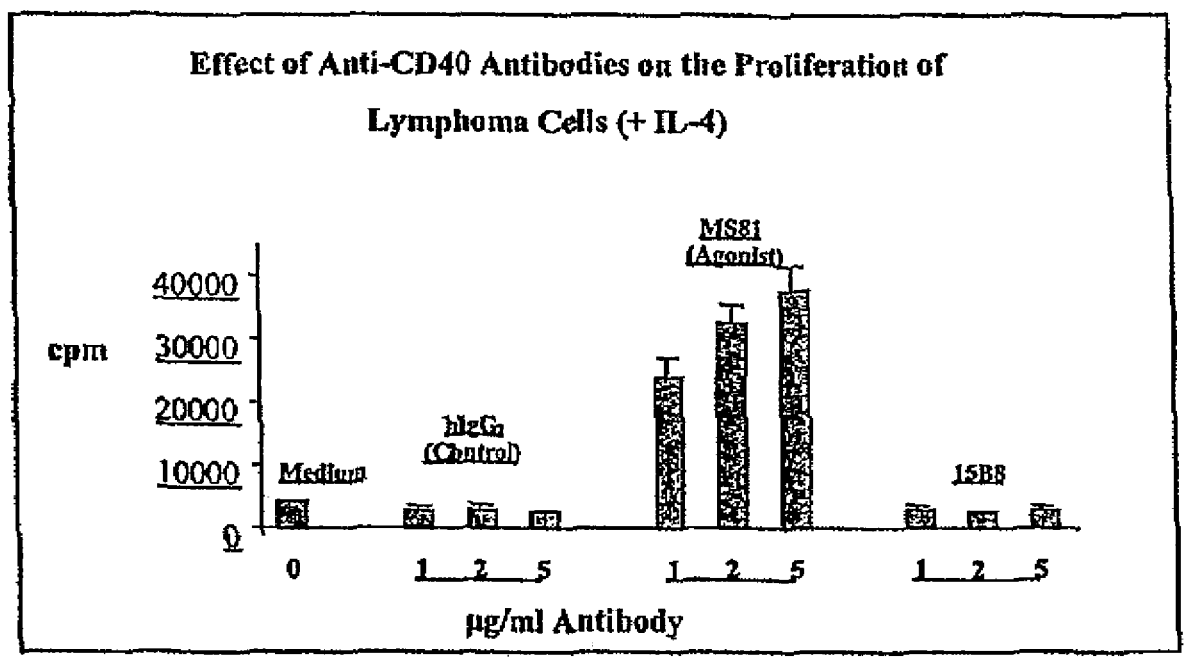
FIG. 2 depicts representative results of the effect of agonist (MS81) and antagonist (15B8) anti-CD40 antibodies at a concentration of 1, 2, or 5 µg/ml on the proliferation of non-Hodgkin's lymphoma (NHL) cells in vitro in the presence of IL-4 (2 ng/ml). Malignant B cells were obtained from tumor infiltrated lymph nodes of a NHL patient. FACS analysis of the NHL cells confirmed that these cells expressed CD40 and bound the antagonist anti-CD40 antibody. See Example 3 below for details.

Anti-CD40 antibody 15B8, at concentrations of 1, 2, and 5 µg/ml, did not stimulate NHL cells to proliferate in either the absence or presence of IL-4. In contrast, an agonistic anti-CD40 antibody (MS81), tested at the same concentration, stimulated NHL-cell proliferation both in the presence and absence of IL-4 in all patient samples. Representative results from one patient are shown in FIGS. 1 and 2. Results from the NHL cells from the two patients in the presence of IL-4 and three patients in the absence of IL-4 were comparable. These results indicate that 15B8 is not an agonist anti-CD40 antibody and does not stimulate proliferation of NHL cells from Rituximab-sensitive, naïve or Rituximab-resistant NHL patients in vitro.

FACS analysis of the NHL cells was performed with either a direct-labeled 15B8-FITC or 15B8 plus anti-huIgG2-FITC to confirm that CD40 is expressed on the surface the NHL cells tested and that 15B8 binds to the NHL cells. The NHL cells from 2 Rituximab-sensitive and 4 Rituximab-resistant patients (6 patients in total) were tested. NHL cells from all the patients expressed CD40 and bound 15B8. The 15B8 binding-positive cell population in any given patient was about 66% to 91%.

Example 4

15B8 Inhibits CD40L-Stimulated Proliferation of NHL Cells In Vitro

To evaluate the ability of 15B8 to block the growth signal provided by CD40L in vitro, NHL cells from patients were cultured as described above in suspension over CD40L-expressing feeder cells under four different conditions: no added antibody (medium); addition of human isotype antibody IgG2 (control); addition of anti-CD40 antibody MS81 (agonistic antibody); and addition of 15B8. All antibodies were added at concentrations of 1, 2, and 5 µg/ml in the presence or the absence of IL-4. The NHL cells from 1 antibody-naïve, 2 Rituximab-sensitive, and 5 Rituximab-resistant patients (8 patients in total) were cultured under the same four conditions as described above in the presence of IL-4 (2 ng/ml). NHL cells from 3 Rituximab-sensitive and 4 Rituximab-resistant patients (7 patients in total) were cultured under similar conditions in the absence of IL-4. The NHL cell proliferation was measured by $^3$H-thymidine incorporation.

Figure 3:
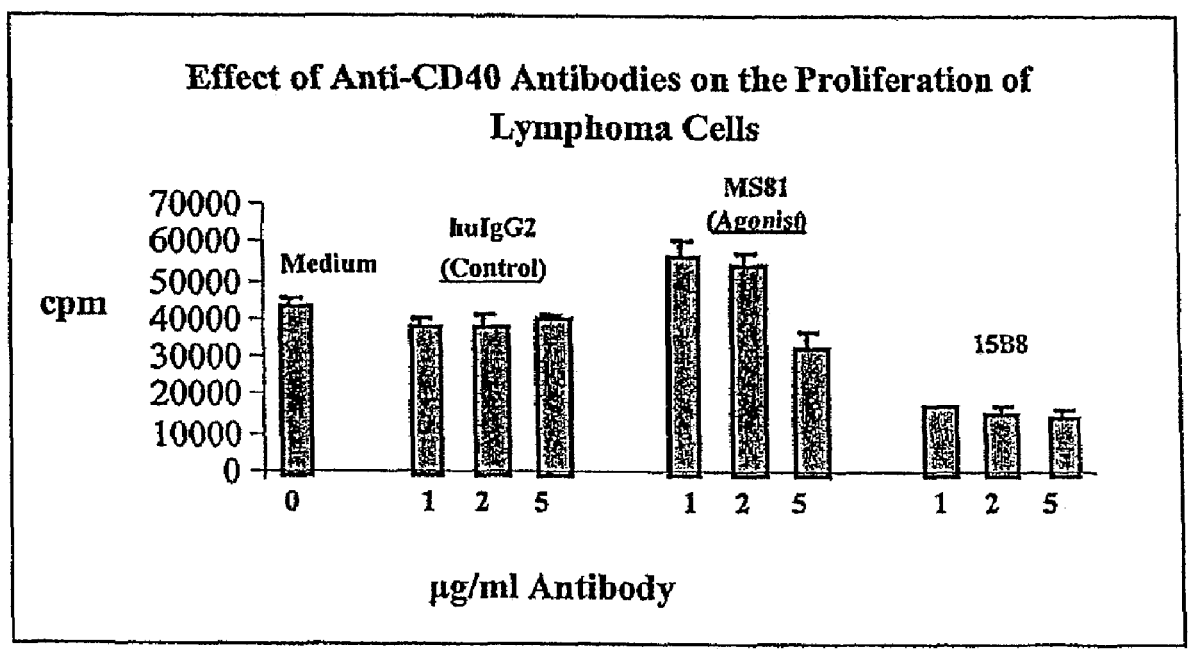
FIG. 3 depicts representative results of the effect of agonist (MS81) and antagonist (15B8) anti-CD40 antibodies at a concentration of 1, 2, or 5 µg/ml on CD40L-stimulated proliferation of NHL cells in vitro in the absence of IL-4. The NHL cells were obtained from a Rituximab-sensitive NHL patient. See Example 4 below for details.

Table 1 below shows the inhibitory effect of 15B8 on the proliferation of NHL cells from 2 Rituximab-sensitive (data from one patient reproducible in two separate experiments) and 4 Rituximab-resistant patients (6 patients in total) stimulated by CD40L alone in vitro. Representative results from the cells of one patient (A) are shown in FIG. 3. 15B8 inhibited the proliferation by about 12-68% when compared to the control in the 6 patients. The degree of inhibition by 15B8 varied depending on patient samples and the dose level of 15B8. Statistical analysis of the data from 6 of the 7 patient samples tested shows that the inhibition of CD40L-stimulated NHL cell proliferation by 15B8 is significant at 1 μg/ml (p=0.05). There is a statistically significant dose response (p<0.005), as the inhibitory effect increases with increasing 15B8 dose.

TABLE 1

Effect of 15B8 MAb on CD40-L stimulation of proliferation of NHL patient cells in the absence of IL-4.[1]

| Patient ID | Patient Type[2] | Treatment Dose (μg/ml) | 15B8 % Inhibition[3] |
|---|---|---|---|
| A | CR | 1 | 56.61 |
|   |    | 2 | 58.99 |
|   |    | 5 | 63.16 |
| A | CR | 1 | 61.96 |
|   |    | 2 | 60.41 |
|   |    | 5 | 64.75 |
|   |    | 10 | 60.29 |
| B | CR | 1 | None |
|   |    | 2 | None |
|   |    | 5 | None |
|   |    | 10 | 12.11 |
| D | NR | 1 | 52.22 |
|   |    | 2 | 61.63 |
|   |    | 5 | 68.04 |
|   |    | 10 | 68.17 |
| E | NR | 1 | 13.07 |
|   |    | 2 | 22.34 |
|   |    | 5 | 31.04 |
|   |    | 10 | 31.87 |
| F | NR | 1 | 24.51 |
|   |    | 2 | 27.43 |
|   |    | 5 | 38.71 |
|   |    | 10 | 47.35 |
| G | NR | 1 | 11.12 |
|   |    | 2 | 22.41 |
|   |    | 5 | 30.61 |
|   |    | 10 | 43.15 |

[1]NHL cells from patients were cultured with murine L-cells expressing human CD40L in the presence of medium, agonist anti-CD40 (MS81), antagonist anti-CD40 (15B8), or huIgG2 isotype control in vitro. The proliferation of the NHL cells was measured by $^3$H-thymidine incorporation (data from one Rituximab-sensitive patient is not in the table for the cpm of CD40L is <2000).
[2]Patient response to anti-CD20 Mab therapy; CR, complete responder; NR, non-responder.
[3]15B8% inhibition = 100 − (15B8 cpm/huIgG2 cpm × 100); represents the mean of 3 determinations.

Figure 4:
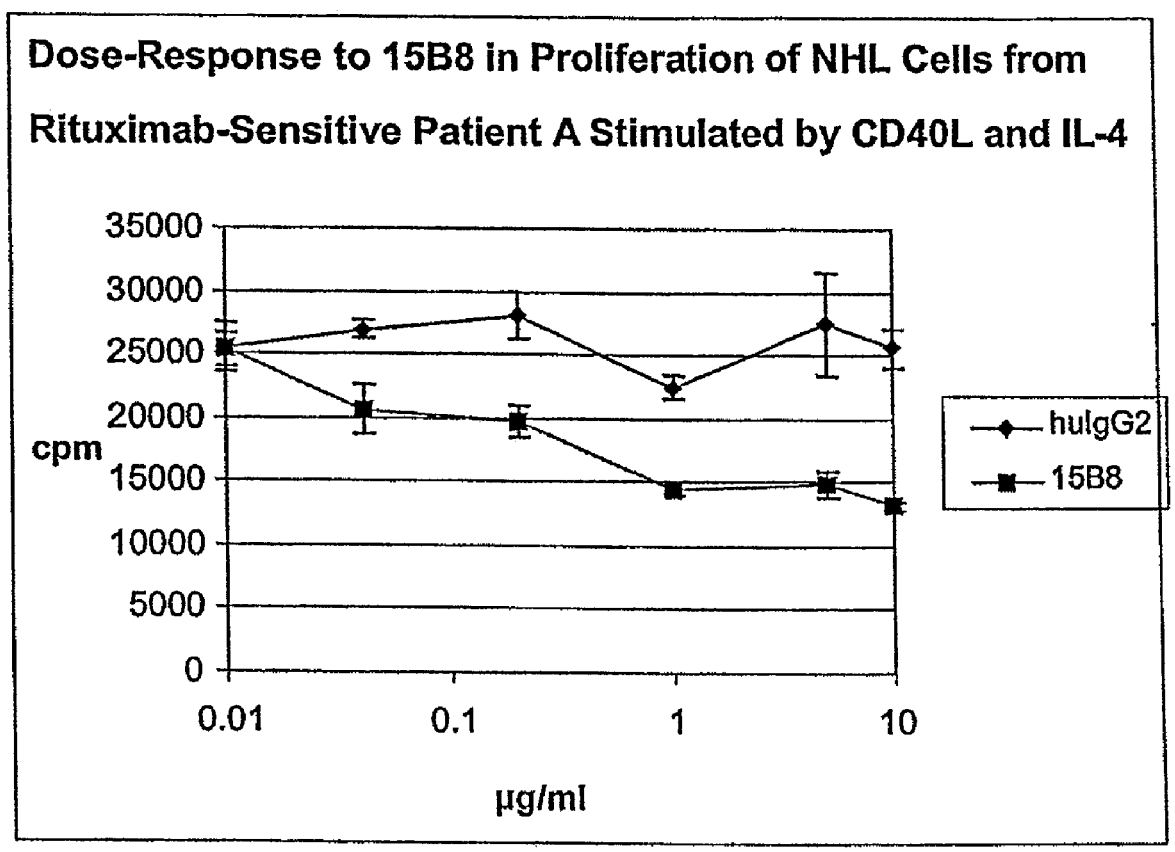
FIG. 4 depicts a representative dose response curve for the antagonist anti-CD40 antibody 15B8 on proliferation of NHL cells stimulated in vitro by CD40L and IL-4 (2 ng/ml). The NHL cells were obtained from a Rituximab-sensitive NHL patient. See Example 4 below for details.

Table 2 (below) shows the inhibitory effect of 15B8 on proliferation of NHL cells from 1 antibody-naïve, 2 Rituximab-sensitive (data from both patient samples were repeated twice reproducibly), and 5 Rituximab-resistant patients (8 patients in total) stimulated by both CD40L and IL-4 in vitro. At 1 μg/ml level, 15B8 significantly (p<0.05) inhibited the CD40L and IL-4-mediated proliferation of the NHL cells. The degree of inhibition ranged from 18-69% at high dose (5 or 10 μg/ml) in samples from all 8 patients in vitro. There was a statistically significant dose response of this inhibitory effect by 15B8 (p<0.005) at a 15B8 concentration range of 0.01-10 μg/ml. FIG. 4 shows one representative dose response curve. These in vitro results suggest that treatment with 15B8 may block the CD40-mediated growth signal for NHL cells in patients.

TABLE 2

Effect of 15B8 Mab on CD40-L stimulation of NHL patient cells in the presence of IL-4.[1]

| Patient ID | Patient Type[2] | Treatment Dose (μg/ml) | 15B8 % Inhibition[3] |
|---|---|---|---|
| A | CR | 1 | 34.39 |
|   |    | 2 | 30.54 |
|   |    | 5 | 36.42 |
| A | CR | 0.01 | 0.44 |
|   |    | 0.04 | 23.32 |
|   |    | 0.2 | 29.54 |
|   |    | 1 | 35.38 |
|   |    | 5 | 46.12 |
|   |    | 10 | 48.63 |
| C | CR | 1 | 34.91 |
|   |    | 2 | 40.89 |
|   |    | 5 | 56.34 |
|   |    | 10 | 69.21 |
| C | CR | 1 | None |
|   |    | 2 | 16.79 |
|   |    | 5 | 21.64 |
|   |    | 10 | 12.63 |
| D | NR | 1 | 1.95 |
|   |    | 2 | 6.43 |
|   |    | 5 | 20.95 |
|   |    | 10 | 26.31 |
| E | NR | 1 | 1.91 |
|   |    | 2 | 2.74 |
|   |    | 5 | 28.36 |
|   |    | 10 | 28.26 |
| E | NR | 1 | None |
|   |    | 2 | 11.76 |
|   |    | 5 | 27.54 |
|   |    | 10 | 34.07 |
| G | NR | 1 | 39.38 |
|   |    | 2 | 32.74 |
|   |    | 5 | 36.48 |
|   |    | 10 | 37.78 |
| H | NR | 1 | None |
|   |    | 2 | None |
|   |    | 5 | 7.81 |
|   |    | 10 | 18.47 |
| I | Naïve | 0.01 | None |
|   |       | 0.04 | 13.16 |
|   |       | 0.2 | 15.64 |
|   |       | 1 | 16.20 |
|   |       | 5 | 21.53 |
|   |       | 10 | 24.51 |

[1]NHL cells from patients were cultured with murine L-cells expressing human CD40L in the presence of IL-4 (human interleukin-4) at 2 ng/ml under conditions described in Table 1.
[2]Patient response to anti-CD20 Mab therapy; CR, complete responder; NR, non-responder; Naïve, untreated.
[3]% inhibition compared to huIgG2. 15B8% inhibition = 100 − (15B8 cpm/huIgG2 cpm × 100).

Example 5

15B8 Does not Activate Human Peripheral Blood B Cells and does not Cause PBMC Proliferation In Vitro in Human, Chimpanzee, and Marmoset To determine if it is an agonist or antagonist anti-CD40, 15B8 was tested in several in vitro assays described below using cells from humans and five different primate species, including chimpanzee (chimp), marmoset, cynomologus monkey, rhesus monkey, and baboon.

to detect cells with positive staining of Annexin V and anti-FasL. There was no significant difference on the surface stain-

TABLE 3

Stimulation of PBMC/B-cell proliferation in human, chimp, and marmoset by 15B8 antibody.[1]

| Species | Cell Source | Number of Samples | Dose (µg/ml) | huIgG2, Base | CD40L, Fold Increase[3] | 15B8, Fold Increase[2] |
|---|---|---|---|---|---|---|
| Human | B | 2 | 5 | 1 | 70.58/36.33 | 1.77/4.37 |
| | | 2 | 1 | 1 | 70.58/36.33 | 3.1/5.4 |
| | | 2 | 0.2 | 1 | 70.58/36.33 | 1.16/4.63 |
| Human | PBMC | 5 | 5 | 1 | 9.36-91.60 | 0.49-2.28 |
| | | 15 | 1 | 1 | 9.36-91.60 | 0.35-2.38 |
| | | 12 | 0.2 | 1 | 9.36-91.60 | 0.41-3.74 |
| Marmoset | PBMC | 3 | 5 | 1 | 29.24-90.3 | 2.05-7.2 |
| Monkey | | 5 | 1 | 1 | 7.99-90.3 | 1.35-5.79 |
| Chimp | PBMC | 1 | 5 | 1 | 10.15 | 2.46 |
| | | 5 | 1 | 1 | 5.12-9.2 | 0.66-5.2 |

[1] B cells/PBMCs were cultured in vitro in the presence of CD40L, 15B8, or huIgG2 isotype control.
[2] Results of the cell proliferation are reported as the ratio of $^3$H-thymidine incorporation for 15B8 to huIgG2 control. Data from some samples are not included in the table for the CPM induced by CD40L (positive control) <2000.
[3] The fold-increase for CD40L shown in the table is the ratio of the CD40L cpm to the cpm of huIgG2 at 5 µg/ml.

Upon B-cell activation, a number of cell surface proteins are up-regulated (Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86). To confirm 15B8 does not activate human B cells and does not induce an agonist signal when bound to CD40, its ability to up-regulate B cell activation markers was tested by FACS analysis using purified human PBMC. There was no up-regulation in the expression of activation markers such as CD25, CD69, CD86, HLA-DR, and ICAM-1 (CD54) in 15B8 treated human B cells (Table 4). The level of these markers was similar when cells were treated with either 15B8 or huIgG2 control (Table 4). In contrast, CD69 was consistently up-regulated by CD40L in PBMC samples from 3 healthy volunteers tested.

ing by the two reagents between cells incubated with 15B8 or the isotype control (huIgG2) antibody (data not shown). This result shows that 15B8 does not induce apoptosis of human B cells in vitro. These data provide further evidence that 15B8 is not an agonist anti-CD40 antibody for human B cells.

15B8 cross-reacts with CD40 expressed on the surface of CD20 positive PBMCs from primates. To test if 15B8 can activate CD40 on B cells from other primate species such as chimpanzees and marmosets, the same proliferation assays were carried out using freshly isolated chimp and marmoset PBMC from 15 chimps and 5 marmosets. Similar to the results with the human PBMC, 15B8 did not stimulate the proliferation in vitro of PBMCs from 6 chimps and 5 marmosets at 1 and 5 µg/ml concentration (Table 3 above). 15B8 also did not up-regulate the expression of activation marker,

TABLE 4

Effect of 15B8 on up-regulation of B-cell activation markers in vitro by FACS.

| Species | Cell Source | Incubation Time | Number of Subjects | CD54 | CD69 | HLA-DR | CD25 | CD80 | CD86 |
|---|---|---|---|---|---|---|---|---|---|
| Human | CD20 from PBMC | 4 h-24 h | 3 | — | — | — | — | N/A | — |
| Chimp | CD20 from PBMC | 4 h-24 h | 3 | N/A | — | N/A | N/A | N/A | N/A |

1. "—" means no up-regulation.
2. "N/A" means not measured or not successful.

Additional consequences of B cell activation are up-regulation of surface FasL and apoptosis (Revy et al. (1998) *Eur. J. Immunol.* 28:3648-3654; Carey et al. (2000) *Immunol. Rev.* 176:105-115; Ju et al. (1999) *Int. Rev. Immunol.* 18:485-513; Baumgarth (2000) *Immunol. Rev.* 176:171-180). To confirm 15B8 is not an agonistic anti-CD40 antibody, its ability to induce FasL expression and apoptosis of human B cells was also tested. Annexin V staining on the cell surface can be used as an early apoptosis marker (Ju et al. (1999) *Int. Rev. Immunol.* 18:485-513). Human B cells were purified from peripheral blood and incubated with 15B8. FACS analysis was used CD69, in the three chimp-PBMC samples tested (Table 4). 15B8 did not show any effect on FasL expression and apoptosis in chimp PBMCs similar to human PBMC controls after 24 and 48 hours stimulation in vitro in all samples from 6 chimps tested (data not shown).

Cross-linking 15B8 by a secondary antibody fixed to plastic surface did not increase its potency to stimulate B-cell proliferation (data not shown). When tested using PBMCs from humans and chimps in this cross-linking assay, 15B8 did not stimulate proliferation of the cells. This observation indicates a reduced risk of 15B8 being stimulative (i.e., agonistic or having agonist activity) for B-cell proliferation in case of induction of anti-15B8 (HAHA) or Fc binding to other Fc receptor expressing cells when administered in vivo.

In summary, 15B8 does not initiate an activation signal in human B cells/PBMCs nor in chimp/marmoset PBMCs in vitro. Therefore, 15B8 is not an agonist anti-CD40 antibody in human, chimps, and marmosets.

Example 6

Figure 5:
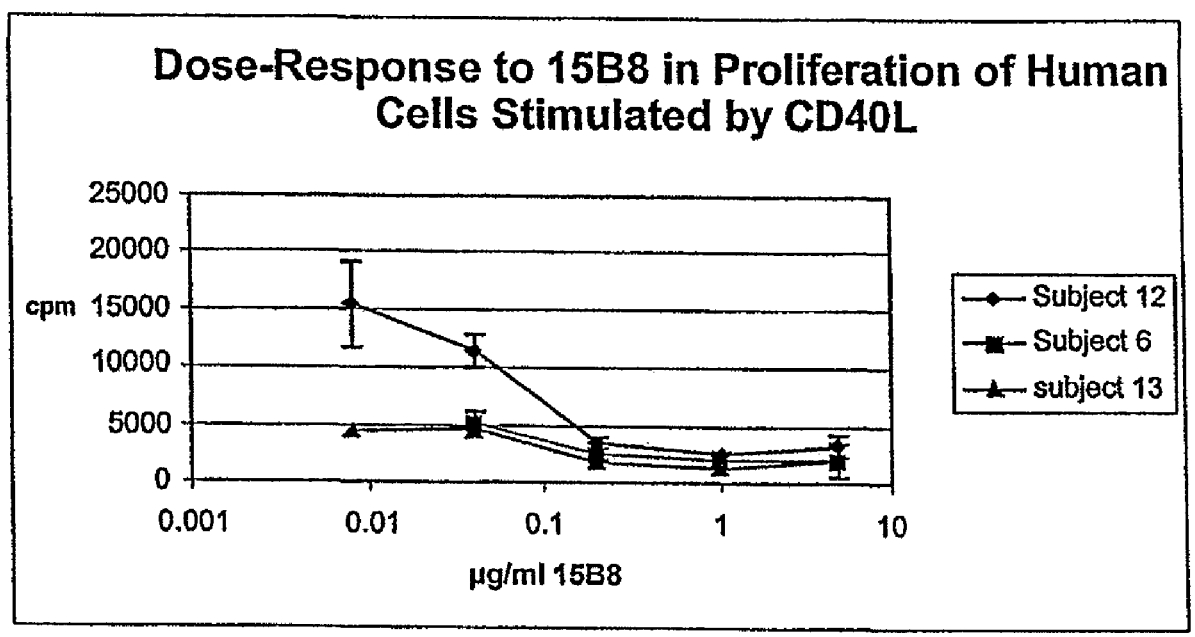
FIG. 5 depicts dose response curves for the antagonist anti-CD40 antibody 15B8 on proliferation of purified human peripheral blood B cells stimulated in vitro in a CD40L-expressing CHO cell-mediated human B-cell proliferation assay. The B cells were obtained from 3 healthy individuals. See Example 6 below for details.

15B8 is an Antagonist Anti-CD40 Antibody in Humans, Chimpanzees, and Marmosets In Vitro To determine if 15B8 is an antagonist anti-CD40, its ability to inhibit CD40-CD40L interaction was tested in a CD40L-mediated human B-cell proliferation assay (Kwekkeboom et al. (1993) *Immunology* 79:439-444). A transfected CHO cell line expressing human CD40L was used to stimulate the proliferation of purified human peripheral blood B cells or PBMCs. Human B cells from 10 healthy volunteers and human PBMCs from 3 healthy volunteers were tested. In all the samples tested, 15B8 suppressed CD40L-expressing CHO cells mediated-proliferation by 42-88% at concentration range from 0.2-5 µg/ml (Table 5). FIG. 5 shows a representative dose-response curve using cells from 3 individuals. The no-effect dose of 15B8 is 0.008 µg/ml and reaches saturating dose at 0.2 µg/ml (FIG. 5). This observation indicates that 15B8, as an antagonist anti-CD40 antibody, can inhibit the growth signals in human B cells and PBMCs provided by cell surface-expressed CD40L.

*Actions Suppl.* 49:17-22; Lederman et al. (1996) *Curr. Opin. Hematol.* 3:77-86; Mackey et al. (1998) *J. Leukoc. Biol.* 63:418-428). To test if 15B8 can block T-helper cell mediated B cell antibody production, purified human peripheral blood B cells were cultured in the presence of purified irradiated T cells activated with anti-CD3 antibody. An ELISA assay was used to measure the level of IgM production. 15B8 reduced IgM production by about 30% in this assay (data not shown). Therefore, 15B8 can reduce T-cell-mediated B-cell immunoglobulin production.

In summary, 15B8 inhibits CD40L-induced B-cell/PBMC proliferation in human, chimp and marmoset, and inhibits T-cell induced antibody production by purified human B cells in vitro. These data demonstrate that 15B8 is an antagonist anti-CD40 antibody in human B cells and PBMCs from chimps and marmosets in vitro.

Example 7

15B8 is an Agonist Anti-Monkey (Cynomologus, Rhesus, and Baboon) CD40 Antibody In Vitro FACS analysis demonstrates that 15B8 binds to CD40 expressed on the surface of B cells from peripheral blood of monkeys (rhesus, cynomologus, and baboon). The effect of 15B8 on freshly isolated cynomologus monkey PBMC was tested in the same proliferation assay described above for human and chimps (Coligan et al. (1998) *Current Protocols in Immunology* 13:12; Kwekkeboom et al. (1993) *Immunol-*

TABLE 5

Inhibition of CD40L-inducted-proliferation of PBMC/B cell with 15B8 antibody.[1]

| Species | Cell Source | Number of Samples | Dose (µg/ml) | CD40L (Base) | HuIgG2, % of Inhibition | 15B8, % of Inhibition[2] |
|---|---|---|---|---|---|---|
| Human | B | 7 | 5 | 100 | (−27)-14% | 45-85% |
|  |  | 9 | 1 | 100 | (−93)-11% | 42-87% |
|  |  | 6 | 0.2 | 100 | (−20)-(−6)% | 44-82% |
| Human | PBMC | 1 | 5 | 100 | 13% | 45% |
|  |  | 2 | 1 | 100 | 3-32% | 76-88% |
| Marmoset Monkey | PBMC | 3 | 1 | 100 | 1-35% | 68-84% |
| Chimpanzee | PBMC | 3 | 1 | 100 | (−3)-21% | 55-73% |

[1]B cells/PBMCs were cultured in vitro with CD40L-expressing CHO cells in the presence of 15B8 or huIgG2 control. CD40L-transfected CHO cells were fixed with formaldehyde before the experiments. The proliferation of cells was measured by $^3$H-thymidine incorporation.
[2]"15B8% inhibition" = 100 − (15B8 cpm/CD40L cpm × 100). Data from some samples are not in the table for proliferation inducted by CD40L (positive control) is <5-fold.

Additional assays were carried out using freshly isolated PBMCs from 9 chimps and 3 marmosets. As with the human PBMCs, 15B8 was able to inhibit the proliferation of chimp and marmoset PBMCs stimulated by CD40L-expressing-CHO cells at 1 µg/ml concentration level (Table 5 above). The inhibition by 15B8 was approximately 55-73% and 68-84% in PBMC samples from 3 chimps and 3 marmosets respectively (Table 5 above).

Activated B cells undergo a number of biological responses such as proliferation and antibody production. The activation of B cells by T cell-dependent antigens involves CD4$^+$ T-helper (Th) cells. This T cell helper process is mediated by a concerted effort of the interaction of CD40 on the B cells with the CD40L on the Th cells surface together with the interactions of other co-stimulatory factors and cytokines (Denton et al. (1998) *Pediatr. Transplant.* 2:6-15; Evans et al. (2000) *J. Immunol.* 164:688-697; Noelle (1998) *Agents*

*ogy* 79:439-444). In contrast to human PBMC, 15B8 was found to stimulate cynomologus monkey PBMC to proliferate in vitro as measured by $^3$H methyl-thymidine incorporation (Table 6 below). At 1 µg/ml level, 15B8 stimulated the proliferation of the PBMCs by 6-fold to 129.7-fold compare to the huIgG2 control in the twenty-two samples from 17 monkeys tested (samples from 5 monkeys were tested twice) (Table 6 below). At 5 µg/ml level, the proliferation stimulated by 15B8 is 14-fold to 24-fold in four samples from 2 monkeys and about 1.25-fold or 1.85-fold in two samples from 2 monkeys (Table 6). This suggests that, at concentration level of 5 µg/ml, 15B8 may be at the limit of over-saturating dose for its proliferation-stimulatory effect on PBMCs from cynomologus monkey. Further FACS analysis of B cells for activation status by surface markers indicated that 15B8 induces CD69, CD86, and HLA-DR up-regulation on monkey B cells (Table 7). These data suggest that 15B8 is an agonist antibody to CD40 expressed on peripheral blood B cells from cynomologus monkeys in vitro.

To confirm that this agonistic effect of 15B8 is not cynomologus-monkey specific, the same assays were performed using PBMCs from rhesus monkeys and baboons. Similar results to that obtained from cells of cynomologus monkeys were observed as shown in Table 6. 15B8 stimulated proliferation of PBMCs from rhesus monkeys and baboons in vitro (Table 6). The agonist activity of 15B8 is shown using the PBMCs from 5 rhesus monkeys and 3 baboons (Table 6).

TABLE 6

Proliferation of PBMCs from human, cynomologus and rhesus monkeys, and baboons stimulated by 15B8.[1]

| Species | Cell Source | Number of Samples | Dose (ug/ml) | huIgG2, Base | CD40L, Fold Increase[3] | 15B8, Fold Increase[2] |
|---|---|---|---|---|---|---|
| Human | PBMC | 5 | 5 | 1 | 9.36-91.60 | 0.49-2.28 |
|  |  | 15 | 1 | 1 | 9.36-91.60 | 0.35-2.38 |
|  |  | 12 | 0.2 | 1 | 9.36-91.60 | 0.41-3.74 |
| Rhesus Monkey | PBMC | 5 | 1 | 1 | 12.71-89.67 | 27.34-50.9 |
| Cyno Monkey | PBMC | 6 | 5 | 1 | 14.57-124.01 | 1.25-24.53 |
|  |  | 22 | 1 | 1 | 5.15-167.73 | 6.13-129.74 |
|  |  | 3 | 0.2 | 1 | 77.01-124.01 | 0.9-67.56 |
| Baboon | PBMC | 3 | 1 | 1 | 5.19-175.07 | 3.32-113.28 |

[1] PBMCs were cultured in vitro in the presence of CD40L, 15B8, or huIgG2 control.
[2] The proliferation results are reported as the ratio of $^3$H-thymidine incorporation for 15B8 to huIgG2 control. Data from some samples are not in the table for the CPM induced by CD40L (positive control) <2000.
[3] The fold-increase for CD40L shown in the table is the ratio of the CD40L cpm to the cpm of huIgG2 at 5 μg/ml. CD40L transfected CHO cells were fixed with formaldehyde before the experiments.

TABLE 7

Effect of 15B8 on upregulation of B-cell activation markers in vitro by FACS analysis.

| Species | Cell source | incubation time | Number of subjects | CD54 | CD69 | HLA-DR | CD25 | CD80 | CD86 |
|---|---|---|---|---|---|---|---|---|---|
| Human | CD20 from PBMC | 4 h-24 h | 3 | — | — | — | — | N/A | — |
| Cyno Monkey | CD20/19 from PBMC | 4 h-3 day | 2 | N/A | ½ up | 1.1 up (day 3) | — | — | 1/1 up (day 3) |

1. "—" means no up-regulation.
2. "N/A" means not measured or not successful.
3. Only cells from one cynomologus monkey was analyzed by FACS on day 3 because of limited cell number.

Example 8

15B8 is an Agonist Anti-CD40 Antibody In Vivo in Cynomologus Monkeys

15B8 can stimulate proliferation and up-regulation of cell surface activation markers in PBMCs from cynomologus monkeys in vitro. To determine if 15B8 is an agonist anti-CD40 antibody in these monkeys in vivo, a study was performed to examine the biodistribution of 15B8 and the fate of affected peripheral B cells (i.e., extravasation, apoptosis, activation status, or complement lysis) [Biodistribution of 15B8.72 Antibodies following Intravenous Administration to Non-Naïve Male and Female Cynomologus Monkeys (SNBL.218.3, SNBL USA)].

Cynomologus monkeys (1 female and 2 males) received a single intravenous administration of 3 mg/kg 15B8. The following parameters were monitored: clinical signs, food consumption, body weight, pharmacokinetics, serum complement (CH50), flow cytometry for B cells (including apoptotic B cells), T cells, and monocytes. B-cell CD40 receptor saturation with 15B8 was also measured. Animals were necropsied 24 hours after receiving the single dose of 15B8, and standard organs were weighed. Pre-study surgical biopsies of spleen and axillary lymph nodes were taken to serve as baseline controls. At necropsy, lymphoid and non-lymphoid tissues were sampled for histopathology and immunohistochemistry. Tissues were immunostained with antibodies against CD3, CD40, CD20, CD27, and CD38 antigens. Preliminary results of the study are discussed below.

All animals survived to the scheduled necropsy and there were no effects on food consumption, body weight, CH50 levels, nor on peripheral blood T-cell or monocyte counts. There were no changes in organ weights. Microscopic examination of the spleen showed moderate diffuse follicular hyperplasia with necrosis and/or neutrophilic infiltrates in the germinal centers of all 15B8-treated animals. Examination of mesenteric and inguinal lymph nodes revealed mild follicular hyperplasia in 2 out of 3 animals. No treatment related microscopic effects were seen in other tissues (liver, skin, brain, thyroid, lung, bone marrow, adrenal gland, and kidney).

Immunostaining with CD20, CD27, CD40, and CD86 antibodies revealed increases in these markers in splenic and lymph node follicles, which correlated with the follicular hyperplasia seen in these same tissues. Increased staining of CD20 and CD40 were limited to the spleen and lymph node while there was some additional staining of hepatic tissue with CD27 and of hepatic Kupffer cells and inflammatory cells by CD86. CD86 staining was also increased in thymic medullary cells and adrenal interstitial leukocytes. There were no changes in the immunostaining of CD3 in 15B8-treated animals as compared to controls.

These findings indicate that a single dose of 3 mg/kg of 15B8 administered to cynomolgus monkey can cause proliferation of lymphoid follicles and/or redistribution of B cells from the peripheral blood in spleen and lymph nodes within a 24-hour period. Antibodies to CD20, CD27, CD40, and CD86 recognize antigens expressed on B cells and/or activated B cells, along with recognition of other cell types. Increased numbers of cells expressing these antigens were seen in the spleen and lymph nodes of treated animals, which suggests an increase in the number of activated CD20+ B cells. This study suggests that 15B8 is an agonist anti-CD40 antibody in cynomologus monkey in vivo. The results obtained in vivo and in vivo are consistent in cynomologus monkeys.

Example 9

Effect of 15B8 on Peripheral B Cells in Chimpanzees

Figure 6:
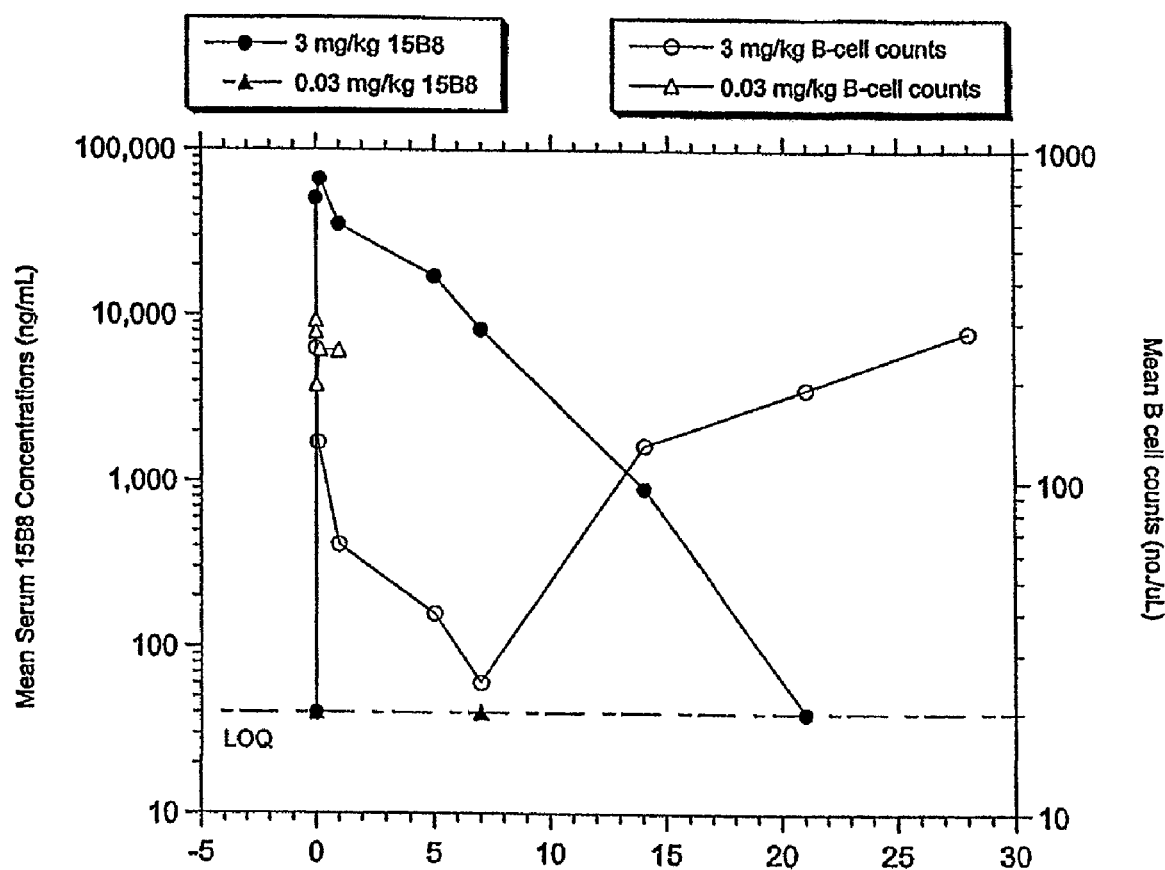
FIG. 6 depicts the effect on the peripheral B-cell count in male chimpanzees after administration of 15B8 at doses of 0.03 or 3 mg/kg. Each dosage level was intravenously administered to 3 chimpanzees, and the average peripheral B-cell count (per µl) was determined (right y-axis). The mean concentration of 15B8 in the serum (ng/ml) is depicted on the left y-axis. Time measured in days relative to the IV administration is shown on the x-axis. After administration of 15B8 at 3 mg/kg, serum 15B8 concentrations declined in a triphasic pattern with a short distribution phase, a log-linear elimination phase, and a non-linear elimination phase. The half-life during the log-linear elimination phase was approximately 4 days. Peripheral B-cell numbers decreased immediately after 15B8 administration and recovered within 3-4 weeks. See Example 9 below for details.

Two groups of 3 male chimpanzees received either 0.03 mg/kg or 3 mg/kg 15B8 by intravenous administration. Serum 15B8 concentrations and peripheral B cell numbers were monitored immediately after 15B8 administration and through day 29 post-dose. The results of the experiment are shown in FIG. 6. After administration of 15B8 at 3 mg/kg, serum 15B8 concentrations declined in a triphasic pattern involving a short distribution phase, a log-linear elimination phase, and a non-linear elimination phase. The non-linear elimination phase predominated at concentrations below approximately 10 μg/ml. The half-life during the log linear phase was approximately four days. Peripheral B cell numbers decreased immediately after 15B8 administration and recovered within 3-4 weeks. 15B8 was detected in serum, bound to surface CD40 receptors on circulating B cells. The extent of binding appeared to remain relatively unchanged from Day 2 through 8 post-dose and declined subsequently through Day 29 post-dose.

After administration of 15B8 at 0.03 mg/kg, B cells appeared to decline slightly by 30 minutes but returned to pre-dose values within 4 hours. Serum 15B8 concentrations were below the level of detection at 30 minutes after dosing.

Example 10

ELISA Assay for Immunoglobulin Quantification

The concentrations of human IgM and IgG are estimated by ELISA assays. 96-well ELISA plates are coated with 4 μg/ml anti-human IgG mAb or with 1.2 μg/ml anti-human IgM mAb in 0.05 M carbonate buffer (pH=9.6) for 16 hours at 4° C. Plates are washed three times with PBS-0.05% Tween-20 (PBS-Tween) and saturated with BSA for one hour. After two washes, the plates are incubated for one hour at 37° C. with different dilutions of the test samples. After three washes, bound Ig is detected by incubation for one hour at 37° C. with 1 μg/ml peroxidase labeled mouse anti-human IgG mAb or mouse anti-human IgM mAb. Plates are washed four times and bound peroxidase activity is revealed by the addition of o-phenylenediamine as a substrate.

CONCLUSIONS

Summary of the In Vitro Assays

The results suggest that 15B8 is an agonistic anti-CD40 antibody in cynomologus and rhesus monkeys and baboons, and an antagonistic antibody in humans, chimpanzees, and marmosets. The experiments that have been completed are summarized in the tables below.

TABLE 8

Assays measuring agonistic activity.

| Assay | Methodology | Species Tested (+ or − Agonistic Activity) |
|---|---|---|
| Effect of 15B8 on B cell proliferation | Compared $^3$H-thymidine incorporation of purified B cells from the peripheral blood in presence of 15B8 with incorporation in presence of CD40L or an agonistic antibody 626.1 | Human (−) |
| Effect of 15B8 on PBMC proliferation | Compared $^3$H-thymidine incorporation of PBMCs in presence of 15B8 with incorporation in presence of CD40L or the isotype control | Human (−) Chimpanzee (−) Cynomologus monkey (+) Rhesus monkey (+) Baboon (+) Marmoset (−) |
| Effect of 15B8 on upregulation of B-cell activation markers | Measured upregulation in the expression of B-cell activation markers in PBMCs stimulated by 15B8 or its isotype control using FACS analysis; compared effect of 15B8 with that of isotype control | Human (−) Chimpanzee (−) Cynomologus monkey (+) Rhesus monkey (+) Baboon (+) Marmoset (−) |
| Effect on PBMC proliferation of 15B8 cross-linked to a secondary antibody fixed to a plastic surface | Compared $^3$H-thymidine incorporation in presence of second Ab-crosslinked 15B8 with incorporation in presence of CD40L 15B8 alone or the isotype control | Human (−) Chimpanzee (−) |

TABLE 8-continued

Assays measuring agonistic activity.

| Assay | Methodology | Species Tested (+ or − Agonistic Activity) |
|---|---|---|
| Effect of 15B8 on upregulation of FasL and apoptosis | Measured upregulation in the expression of FasL and apoptosis by FACS detection of B cells with positive staining of anti-FasL and Annexin V (marker for apoptosis) by the stimulation of CD40L, 15B8, and the isotype control. | Human (−) Chimps (−) Cynomologus Monkey (−/+) |

TABLE 9

Assays measuring antagonistic activity.

| Assay | Methodology | Species Tested (+ or − Antagonistic Activity) |
|---|---|---|
| Inhibition by 15B8 of CD40L-mediated B-cell proliferation | Stimulation of B-cell proliferation by CD40L-expressing CHO cells was measured by $^3$H-thymidine incorporation. Compared $^3$H-thymidine incorporation in presence of 15B8 with that in presence of isotype control | Human (+) Marmoset (+) Chimps (+) |
| Inhibition by 15B8 of T-helper-cell-mediated B-cell antibody production | B cells were cultured with purified irradiated T cells activated with anti-CD3 antibody in the presence of 15B8. The level of B-cell IgM production was assessed by ELISA. | Human (+) |

15B8 is an anti-human CD40 specific monoclonal antibody with human IgG$_2$ subtype and with cross-reactivity to CD40 from non-human primates only. Through extensive in vitro testing, 15B8 was shown to be an antagonist anti-CD40 to the CD40 expressed on human B cells, PBMCs from human, chimp, and marmoset. However, 15B8 was shown to have agonist activity when bound to the CD40 expressed on PBMCs from monkeys (cynomologus, rhesus, and baboon) in vitro. This agonist activity of 15B8 was confirmed in vivo in cynomologus monkeys. When tested in primary culture of lymphoma cells from Rituxan™-sensitive and resistant NHL patients, 15B8 has no agonist activity in the presence or absence of IL-4. 15B8 can also inhibit CD40L-stimulated growth of the lymphoma cells from the similar group of patients under both conditions. 15B8 has the potential to modify B-cell malignancies, such as non-Hodgkin's lymphoma (NHL), where the CD40/CD40L pathway may play a role in the pathogenesis of the diseases.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

That which is claimed:

1. A conjugated human anti-CD40 monoclonal antibody or a conjugated antigen-binding fragment thereof, wherein said conjugated anti-CD40 antibody or conjugated fragment thereof exhibits antagonist activity when said conjugated antibody or conjugated fragment thereof binds a CD40 antigen on a malignant human B cell, wherein said conjugated antibody comprises an antibody selected from the group consisting of:
   a) the monoclonal antibody produced by the hybridoma cell line 15B8 (Patent Deposit Designation PTA-3814);
   b) a monoclonal antibody comprising a light chain variable region having the amino acid sequence set forth in SEQ ID NO:2 and a heavy chain variable region having the amino acid sequence set forth in SEQ ID NO:4; and
   c) a monoclonal antibody having a light chain variable region having the amino acid sequence encoded by the nucleotide sequence set forth in SEQ ID NO:1 and a heavy chain variable region having the amino acid sequence encoded by the nucleotide sequence set forth in SEQ ID NO:3;

wherein said conjugated antigen-binding fragment of said conjugated antibody retains the capability of specifically binding to human CD40.

2. The conjugated human anti-CD40 monoclonal antibody of claim 1, wherein said conjugated antibody comprises the monoclonal antibody produced by hybridoma cell line 15B8 (Patent Deposit Designation PTA-3814).

3. The conjugated human anti-CD40 monoclonal antibody of claim 1, wherein said conjugated antigen-binding fragment thereof is selected from the group consisting of a Fab fragment, an F(ab')₂ fragment, and Fv fragment, and a single-chain Fv fragment.

4. A pharmaceutical composition comprising the conjugated human anti-CD40 monoclonal antibody of claim 1 or a conjugated antigen-binding fragment thereof.

5. A method for treating a patient with a disease comprising malignant B cells, said method comprising administration of a therapeutically effective amount of a conjugated human anti-CD40 monoclonal antibody or a conjugated antigen-binding fragment thereof to said patient, wherein said conjugated anti-CD40 antibody or conjugated fragment thereof exhibits antagonist activity when said conjugated antibody or conjugated fragment thereof binds a CD40 antigen on a malignant human B cell, wherein said conjugated human anti-CD40 monoclonal antibody comprises an antibody selected from the group consisting of:
  a) the monoclonal antibody produced by the hybridoma cell line 15B8 (Patent Deposit Designation PTA-3814);
  b) a monoclonal antibody comprising a light chain variable region having the amino acid sequence set forth in SEQ ID NO:2 and a heavy chain variable region having the amino acid sequence set forth in SEQ ID NO:4; and
  c) a monoclonal antibody having a light chain variable region having the amino acid sequence encoded by the nucleotide sequence set forth in SEQ ID NO:1 and a heavy chain variable region having the amino acid sequence encoded by the nucleotide sequence set forth in SEQ ID NO:3;

wherein said conjugated antigen-binding fragment of said conjugated antibody retains the capability of specifically binding to human CD40, and whereby said disease is treated.

6. The method of claim 5, wherein said malignant B cells are selected from the group consisting of B-cell lymphoma cells, non-Hodgkin's lymphoma cells, high-grade B-cell lymphoma cells, intermediate-grade B-cell lymphoma cells, low-grade B-cell lymphoma cells, B-cell acute lymphoblastic leukemia cells, multiple myeloma cells, chronic lymphocytic leukemia cells, myeloblastic leukemia cells, and Hodgkin's disease cells.

7. The method of claim 5, wherein said conjugated antigen-binding fragment is selected from the group consisting of a Fab fragment, an F(ab')$_2$ fragment, and Fv fragment, and a single-chain Fv fragment.

8. A method of inhibiting proliferation of malignant cells of B cell lineage, said method comprising contacting said malignant cells with an effective amount of a conjugated human anti-CD40 monoclonal antibody or conjugated antigen-binding fragment thereof, whereby when said conjugated antibody or conjugated fragment thereof binds to CD40 antigen on said malignant cells, the proliferation of said malignant cells is inhibited, wherein said conjugated human anti-CD40 monoclonal antibody comprises an antibody selected from the group consisting of:
  a) the monoclonal antibody produced by the hybridoma cell line 15B8 (Patent Deposit Designation PTA-3814);
  b) a monoclonal antibody comprising a light chain variable region having the amino acid sequence set forth in SEQ ID NO:2 and a heavy chain variable region having the amino acid sequence set forth in SEQ ID NO:4; and
  c) a monoclonal antibody having a light chain variable region having the amino acid sequence encoded by the nucleotide sequence set forth in SEQ ID NO:1 and a heavy chain variable region having the amino acid sequence encoded by the nucleotide sequence set forth in SEQ ID NO:3;

wherein said conjugated antigen-binding fragment of said conjugated antibody retains the capability of specifically binding to human CD40.

9. The method of claim 8, wherein said malignant cells are selected from the group consisting of B-cell lymphoma cells, non-Hodgkin's lymphoma cells, high-grade B-cell lymphoma cells, intermediate-grade B-cell lymphoma cells, low-grade B-cell lymphoma cells, B-cell acute lymphoblastic leukemia cells, multiple myeloma cells, chronic lymphocytic leukemia cells, myeloblastic leukemia cells, and Hodgkin's disease cells.

\* \* \* \* \*

SEQUENCE LISTING

```
<160> NUMBER OF SEQ ID NOS: 4

<210> SEQ ID NO 1
<211> LENGTH: 336
<212> TYPE: DNA
<213> ORGANISM: Homo sapiens
<220> FEATURE:
<221> NAME/KEY: CDS
<222> LOCATION: (1)...(336)

<400> SEQUENCE: 1 gat att gtg atg acc cag tct cca ctc tct ctg tcc gtc gcc cct gga      48
```

```
Asp Ile Val Met Thr Gln Ser Pro Leu Ser Leu Ser Val Ala Pro Gly
 1               5                  10                  15 cag ccg gcc tcc atc tcc tgt aag tct agt cag agc ctc ctg gag agt       96
Gln Pro Ala Ser Ile Ser Cys Lys Ser Ser Gln Ser Leu Leu Glu Ser
             20                  25                  30 tat gga gag acc tat ttg tat tgg tac ctg cag aag cca ggc cag cct      144
Tyr Gly Glu Thr Tyr Leu Tyr Trp Tyr Leu Gln Lys Pro Gly Gln Pro
         35                  40                  45 cca cag ctc ctg atc tat gca gtt ttt aag cgg ttc tct gga gtg cca      192
Pro Gln Leu Leu Ile Tyr Ala Val Phe Lys Arg Phe Ser Gly Val Pro
     50                  55                  60 gat agg ttc agt ggc agc ggg tca ggg aca gat ttc aca ctg aaa atc      240
Asp Arg Phe Ser Gly Ser Gly Ser Gly Thr Asp Phe Thr Leu Lys Ile
 65                  70                  75                  80 agc cgg gtg gag gct gag gat gtt ggg gtt tat tac tgc atg caa agt      288
Ser Arg Val Glu Ala Glu Asp Val Gly Val Tyr Tyr Cys Met Gln Ser
                 85                  90                  95 atg cag ctt cct ctc act ttc ggc gga ggg acc aag gtg gag atc aaa      336
Met Gln Leu Pro Leu Thr Phe Gly Gly Gly Thr Lys Val Glu Ile Lys
             100                 105                 110
```

<210> SEQ ID NO 2
<211> LENGTH: 112
<212> TYPE: PRT
<213> ORGANISM: Homo sapiens

<400> SEQUENCE: 2

```
Asp Ile Val Met Thr Gln Ser Pro Leu Ser Leu Ser Val Ala Pro Gly
 1               5                  10                  15

Gln Pro Ala Ser Ile Ser Cys Lys Ser Ser Gln Ser Leu Leu Glu Ser
             20                  25                  30

Tyr Gly Glu Thr Tyr Leu Tyr Trp Tyr Leu Gln Lys Pro Gly Gln Pro
         35                  40                  45

Pro Gln Leu Leu Ile Tyr Ala Val Phe Lys Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Met Gln Leu Pro Leu Thr Phe Gly Gly Gly Thr Lys Val Glu Ile Lys
             100                 105                 110
```

<210> SEQ ID NO 3
<211> LENGTH: 366
<212> TYPE: DNA
<213> ORGANISM: Homo sapiens
<220> FEATURE:
<221> NAME/KEY: CDS
<222> LOCATION: (1)...(366)

<400> SEQUENCE: 3

```
cag gtg cag ctg cag gag tct ggg gga ggc gtg gtc cag cct ggg agg       48
Gln Val Gln Leu Gln Glu Ser Gly Gly Gly Val Val Gln Pro Gly Arg
 1               5                  10                  15 tcc ctg aga ctc tcc tgt gca gcc tct gga ttc acc ttc aat aac ttt       96
Ser Leu Arg Leu Ser Cys Ala Ala Ser Gly Phe Thr Phe Asn Asn Phe
             20                  25                  30 ggc ata cac tgg gtc cgc cag gct cca ggc aag ggg ctg gag tgg gtg      144
Gly Ile His Trp Val Arg Gln Ala Pro Gly Lys Gly Leu Glu Trp Val
         35                  40                  45
```

```
gca gtt ata tca tat gat gga agt gat aaa tat tat gca gac tcc gtg    192
Ala Val Ile Ser Tyr Asp Gly Ser Asp Lys Tyr Tyr Ala Asp Ser Val
    50                  55                  60 aag ggc cga ttc acc atc tcc aga gac aat tcc aag aac acg ctg aat    240
Lys Gly Arg Phe Thr Ile Ser Arg Asp Asn Ser Lys Asn Thr Leu Asn
 65                  70                  75                  80 ctg caa atg aat agt ctg aga gct gag gac acg gct gtg tat tac tgt    288
Leu Gln Met Asn Ser Leu Arg Ala Glu Asp Thr Ala Val Tyr Tyr Cys
                 85                  90                  95 gcg aga gat cgt cgg tat tac tac cac tac tac ggt atg gac gtc tgg    336
Ala Arg Asp Arg Arg Tyr Tyr Tyr His Tyr Tyr Gly Met Asp Val Trp
            100                 105                 110 ggc caa ggg acc atg gtc acc gtc tcc tca                            366
Gly Gln Gly Thr Met Val Thr Val Ser Ser
        115                 120

<210> SEQ ID NO 4
<211> LENGTH: 122
<212> TYPE: PRT
<213> ORGANISM: Homo sapiens

<400> SEQUENCE: 4

Gln Val Gln Leu Gln Glu Ser Gly Gly Val Val Gln Pro Gly Arg
 1               5                  10                  15

Ser Leu Arg Leu Ser Cys Ala Ala Ser Gly Phe Thr Phe Asn Asn Phe
                20                  25                  30

Gly Ile His Trp Val Arg Gln Ala Pro Gly Lys Gly Leu Glu Trp Val
            35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Ala Glu Asp Thr Ala Val Tyr Tyr Cys
                 85                  90                  95

Ala Arg Asp Arg Arg Tyr Tyr Tyr His Tyr Tyr Gly Met Asp Val Trp
            100                 105                 110

Gly Gln Gly Thr Met Val Thr Val Ser Ser
        115                 120
```